United States Patent [19]
Wilcox et al.

[11] Patent Number: 6,040,444
[45] Date of Patent: Mar. 21, 2000

[54] PROCESS FOR PREPARING FURAN NITRONE COMPOUNDS

[75] Inventors: Allan L. Wilcox, Mountain View; Yong-Kang Zhang, Santa Clara, both of Calif.

[73] Assignee: Centaur Pharmaceuticals, Inc., Sunnyvale, Calif.

[21] Appl. No.: 09/317,267

[22] Filed: May 24, 1999

Related U.S. Application Data

[62] Division of application No. 08/895,968, Jul. 17, 1997
[60] Provisional application No. 60/022,169, Jul. 19, 1996.

[51] Int. Cl.⁷ ............... C07D 307/52; C07D 405/12; C07D 413/12
[52] U.S. Cl. ............. 544/152; 544/374; 549/475; 549/476
[58] Field of Search ................ 549/475, 476; 544/152, 374

[56] References Cited

U.S. PATENT DOCUMENTS

| | | | |
|---|---|---|---|
| 3,666,754 | 5/1972 | Minami et al. | 424/285 |
| 3,834,073 | 9/1974 | Dorschner et al. | 47/57.6 |
| 3,849,934 | 11/1974 | Dorschner et al. | 47/57.6 |
| 3,903,049 | 9/1975 | Saltman et al. | 260/47 |
| 3,917,700 | 11/1975 | Auerbach | 260/566 |
| 3,950,327 | 4/1976 | Eschenmoser | 260/240 G |
| 3,988,159 | 10/1976 | Schlesinger | 96/88 |
| 4,153,722 | 5/1979 | Campbell et al. | 424/304 |
| 4,411,978 | 10/1983 | Laridon et al. | 430/157 |
| 4,803,282 | 2/1989 | St. Georgiev et al. | 548/336 |
| 4,871,862 | 10/1989 | Georgiev et al. | 548/262 |
| 5,292,746 | 3/1994 | Carr et al. | 514/278 |
| 5,352,442 | 10/1994 | Proctor | 424/70 |
| 5,397,789 | 3/1995 | Carr et al. | 514/309 |
| 5,455,272 | 10/1995 | Janzen et al. | 514/579 |
| 5,482,966 | 1/1996 | Bird et al. | 514/456 |
| 5,532,252 | 7/1996 | Carr et al. | 514/309 |
| 5,723,502 | 3/1998 | Proctor | 514/741 |
| 5,780,510 | 7/1998 | Carney | 514/576 |

FOREIGN PATENT DOCUMENTS

| | | |
|---|---|---|
| 0 327 263 B1 | 9/1994 | European Pat. Off. |
| 2137619A | 10/1984 | United Kingdom. |
| WO 91/05552 | 5/1991 | WIPO. |
| WO 92/22290 | 12/1992 | WIPO. |
| WO 95/17876 | 7/1995 | WIPO. |
| WO 97/19054 | 5/1997 | WIPO. |
| WO 98/13332 | 4/1998 | WIPO. |

OTHER PUBLICATIONS

Fevig et al., Synthesis, and in vitro Evaluation of Cyclic Nitrones as Free Radical Traps for the Treatment of Stroke, J. Med. Chem., vol. 39, No. 25, pp. 4988–4996, 1996.
Fevig, Thomas L., et al. *Journal of Medicinal Chemistry*, (1996) 39, 4988–4996.
P. Proctor, *Physiol. Chem. & Physics.* (1974) 4, 349–360.
P. H. Proctor, et al., *Physiological Chemistry and Physics and Medical NMR.* (1984) 16, 175–195.
P. Proctor, *CRC Handbook of Free Radicals and Antioxidants.* (1989) 1, 209–221.

*Primary Examiner*—Mukund J. Shah
*Assistant Examiner*—Deepak R. Rao
*Attorney, Agent, or Firm*—Burns, Doane, Swecker & Mathis LLP

[57] ABSTRACT

Disclosed are processes for preparing furan nitrone compounds using a furan carbonyl compound and a hydroxylamine compound.

16 Claims, 5 Drawing Sheets

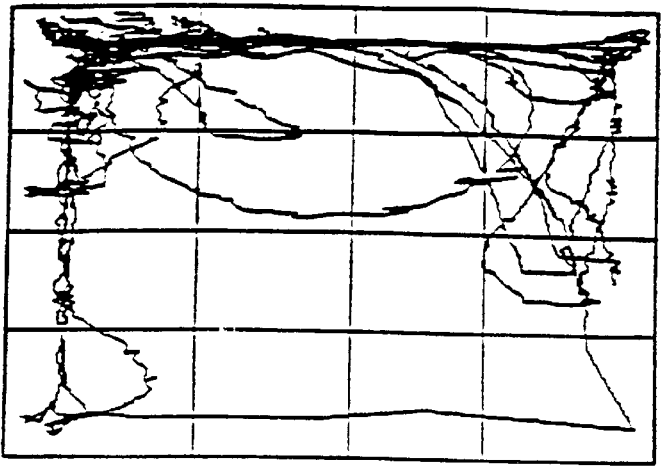
FIG. 3A 1% METHYLCELLULOSE / SALINE
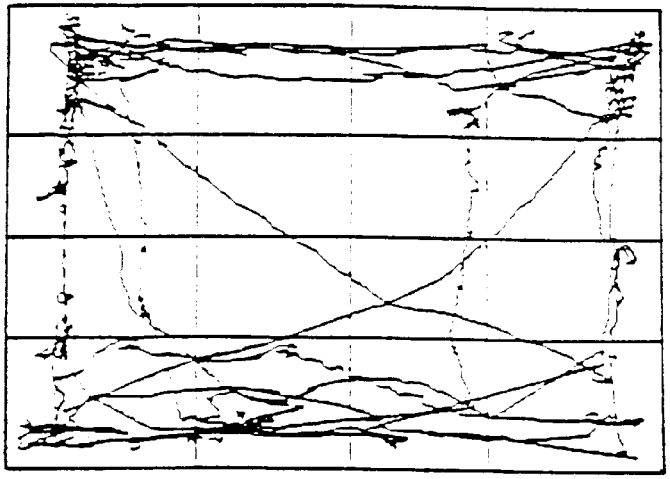
FIG. 3B 1% METHYLCELLULOSE / NITROARGININE
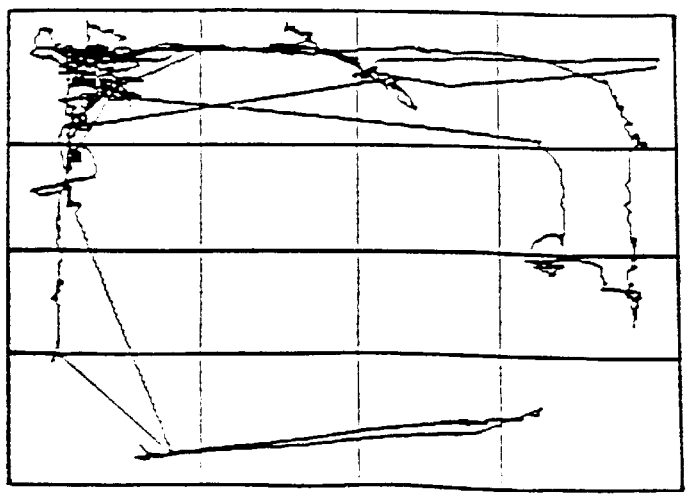
FIG. 3C 10 mg/kg COMPOUND 1 / NITROARGININE

PROCESS FOR PREPARING FURAN NITRONE COMPOUNDS

CROSS-REFERENCE TO RELATED APPLICATIONS

This application is a divisional of U.S. Ser. No. 08/895,968, filed Jul. 17, 1997, which application claims priority to U.S. Ser. No. 60/022,169, filed Jul. 19, 1996; the disclosures of which are incorporated by reference in their entirety.

BACKGROUND OF THE INVENTION

1. Field of the Invention

This invention relates to novel furan nitrone compounds and their use as free radical trapping agents and therapeutic agents. More particularly, this invention concerns furan nitrone compounds and their use as analytical reagents for detecting free radicals and as therapeutics for treating various medical dysfunctions and diseases.

2. State of the Art

Nitrones, such as α-phenyl-N-tert-butylnitrone (PBN) and 5,5-dimethyl-1-pyrroline-N-oxide (DMPO), are known to be useful as analytical reagents for detecting free radicals. Such compounds function as "spin traps" by reacting with unstable free radicals to form relatively stable free radical spin adducts which are observable by electron spin resonance (ESR) spectroscopy. Thus, spin trapping allows previously unobservable free radicals to be identified and studied using ESR and related techniques.

The use of nitrones as spin traps for studying unstable free radicals has been applied to biological systems. In this regard, PBN, DMPO and related compounds have been used to identify superoxide ($O_2^-$.) and hydroxyl radicals (HO.) in biological systems. Additionally, such nitrones have been used to study lipid peroxidation and other free radical-induced biological processes.

More recently, nitrone compounds, such as PBN and derivatives thereof, have been reported as therapeutics for the treatment of a wide variety of disease conditions arising from or characterized by free radical-induced oxidative damage. Such disease conditions include, for example, disorders of the central nervous system (CNS) and the peripheral nervous system, such as stroke, Parkinsonism, traumatic nerve damage and the like, and disorders of the peripheral organs, such as atherosclerosis, cardiac infarction, ulcerative colitis and the like. Nitrones have also been reported to treat certain inflammatory conditions, such as arthritis.

Although various nitrone compounds have been previously reported to be useful as analytical reagents or therapeutic agents, a need exists for novel nitrone spin traps having improved effectiveness in these applications. For example, when using nitrones as therapeutic agents for treating acute conditions, such as stroke, cardiac infarction or the like, it is particularly desirable to be able to administer the nitrone spin trap at high doses, especially to the localized area immediately surrounding the acute incident, to minimize the amount of free radical-induced oxidative damage that occurs. Thus, nitrone compounds used to treat acute conditions should be non-toxic or have very low toxicity.

Additionally, when studying free radicals in biological systems or when treating various disease conditions caused by free radicals, it is important that the nitrone spin trap have sufficient solubility at the biological site where the free radicals are generated so that the radicals are trapped by the nitrone before they are quenched or cause oxidative damage by their surroundings. Thus, it would be particularly desirable to be able to readily optimize the solubility of nitrone compounds for a particular biological environment ranging in nature, for example, from aqueous to lipophilic.

Accordingly, a need exists for new classes of effective nitrone spin traps having improved properties such as low toxicity and increased solubility in a wide range of biological systems.

SUMMARY OF THE INVENTION

This invention provides novel furan nitrone compounds which are effective free radical spin traps and, accordingly, are useful as analytical reagents for detecting free radicals. Additionally, the furan nitrones of this invention have been found to be useful as therapeutics for treating various medical dysfunctions and diseases. In this regard, the furan nitrone compounds have surprisingly low toxicity even at relatively high dosage levels. Structurally, the furan nitrones of this invention are particularly useful as analytical reagents and/or therapeutics since one or more sulfur derived functional groups are attached to the furan ring thereby allowing the lipophilicity of the compounds to be readily varied. This permits the compounds to be used in a wide variety of biological environments and/or optimized for a particular analytical or therapeutic use.

Accordingly, in one of its composition aspects, this invention is directed to compounds of formula I:

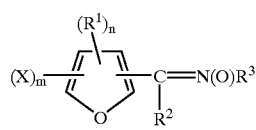

wherein each $R^1$ is independently selected from the group consisting of hydrogen, alkyl, substituted alkyl, alkenyl, alkynyl, alkaryl, aryl, alkoxy, alkcycloalkyl, cycloalkyl, cycloalkenyl and halo;

$R^2$ is selected from the group consisting of hydrogen, alkyl, substituted alkyl, alkenyl, alkynyl, alkaryl, aryl, alkcycloalkyl, cycloalkyl and cycloalkenyl;

$R^3$ is selected from the group consisting of alkyl, substituted alkyl, alkenyl, alkynyl, alkaryl, aryl, alkcycloalkyl, cycloalkyl and cycloalkenyl;

each X is independently selected from the group consisting of —$SO_3Y$, —$S(O)R^4$, —$SO_2R^5$ and —$SO_2NR^6R^7$;

wherein Y is hydrogen or a pharmaceutically acceptable cation;

$R^4$ is selected from the group consisting of alkyl, substituted alkyl, alkenyl, alkynyl, alkaryl, aryl, alkcycloalkyl, cycloalkyl and cycloalkenyl;

$R^5$ is selected from the group consisting of alkyl, substituted alkyl, alkenyl, alkynyl, alkaryl, aryl, alkcycloalkyl, cycloalkyl and cycloalkenyl;

$R^6$ and $R^7$ are independently selected from the group consisting of hydrogen, alkyl, substituted alkyl, alkenyl, alkynyl, alkaryl, aryl, alkcycloalkyl, cycloalkyl and cycloalkenyl; or $R^6$ and $R^7$ together with the nitrogen atom to which they are attached can form a heterocyclic ring containing from 2 to 8 carbon atoms and optionally from 1 to 3 additional heteroatoms selected from the group consisting of oxygen, nitrogen and sulfur;

m is an integer from 1 to 3; and n is an integer from 0 to 2, provided that m+n=3; or pharmaceutically acceptable salts thereof.

Preferably, in the compounds of formula I above, $R^1$ is selected from the group consisting of hydrogen and alkyl. More preferably, $R^1$ is hydrogen.

$R^2$ is preferably selected from the group consisting of hydrogen, alkyl and aryl. More preferably, $R^2$ is hydrogen or alkyl. Still more preferably, $R^2$ is hydrogen.

Preferably, $R^3$ is selected from the group consisting of alkyl, alkaryl, aryl and cycloalkyl. More preferably, $R^3$ is alkyl or cycloalkyl. Still more preferably, $R^3$ is cycloalkyl. Especially preferred $R^3$ groups are cyclohexyl and isopropyl.

$R^4$ is preferably selected from the group consisting of alkyl, alkaryl, aryl and cycloalkyl. More preferably, $R^4$ is alkyl, aryl or cycloalkyl. Still more preferably, $R^4$ is alkyl.

Preferably, $R^5$ is selected from the group consisting of alkyl, alkaryl, aryl and cycloalkyl. More preferably, $R^5$ is alkyl, aryl or cycloalkyl. Still more preferably, $R^5$ is alkyl.

X is preferably $-SO_3Y$, $-SO_2R^5$ or $-SO_2NR^6R^7$, wherein $R^5$ is alkyl, cycloalkyl or aryl and $R^6$ and $R^7$ are independently selected from the group consisting of hydrogen, alkyl and cycloalkyl. Alternatively, $R^6$ and $R^7$ are preferably joined together with the nitrogen atom to which they are attached to form a heterocyclic ring having 4 to 6 carbon atoms. More preferably, when X is $-SO_2NR^5R^6$, $R^5$ is hydrogen and $R^6$ is selected from the group consisting of hydrogen, alkyl and cycloalkyl.

Preferably, m in formula I above is 1 or 2. More preferably, m is 1.

In another of its composition aspects, this invention is directed to a compound of formula II:

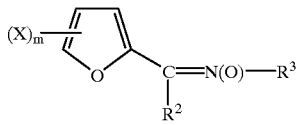

II wherein $R^2$, $R^3$, X and m are as defined above, including the above defined preferred embodiments; or pharmaceutically acceptable salts thereof.

In still another of its composition aspects, this invention is directed to a compound of formula III:

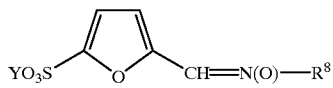

III wherein $R^8$ is selected from the group consisting of alkyl, substituted alkyl, alkenyl, alkynyl, alkaryl, aryl, alkcycloalkyl, cycloalkyl and cycloalkenyl; and Y selected from the group consisting of hydrogen and a pharmaceutically acceptable cation.

Preferably, in formula III above, $R^8$ is selected from the group consisting of alkyl, alkaryl, aryl and cycloalkyl. More preferably, $R^8$ is alkyl or cycloalkyl. Still more preferably, $R^8$ is alkyl.

Preferably, in formula III above, Y is hydrogen or a sodium cation.

In yet another of its composition aspects, this invention is directed to the following individual compounds:

N-isopropyl-α-(2-sulfofuran-5-yl)nitrone
N-n-propyl-α-(2-sulfofuran-5-yl)nitrone
N-n-butyl-α-(2-sulfofuran-5-yl)nitrone
N-tert-butyl-α-(2-sulfofuran-5-yl)nitrone
N-n-hexyl-α-(2-sulfofuran-5-yl)nitrone
N-cyclohexyl-α-(2-sulfofuran-5-yl)nitrone
N-tert-octyl-α-(2-sulfofuran-5-yl)nitrone
N-benzyl-α-(2-sulfofuran-5-yl)nitrone
N-isopropyl-α-[2-(N-morpholinosulfonyl)furan-5-yl] nitrone
N-isopropyl-α-[2-(N,N-dimethylsulfamoyl)furan-5-yl] nitrone
N-isopropyl-α-[2-(N,N-diethylsulfamoyl)furan-5-yl] nitrone
N-isopropyl-α-[2-(N-4-methylpiperazin-1-ylsulfonyl) furan-5-yl]nitrone
N-tert-butyl-α-[2-(N-3-trifluoromethylphenylsulfamoyl)-furan-5-yl]nitrone
N-tert-butyl-α-[2-(methylsulfonyl)-furan-5-yl]nitrone, and pharmaceutically acceptable salts thereof.

This invention is also directed to pharmaceutical compositions comprising a pharmaceutically acceptable carrier and a pharmaceutically effective amount of a compound of formula I:

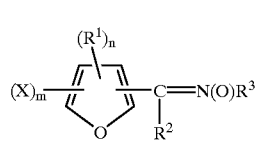

I wherein $R^1-R^3$, X, m and n are as defined above; or pharmaceutically acceptable salts thereof.

In additional composition aspects, this invention is directed to pharmaceutical compositions comprising a pharmaceutically acceptable carrier and a pharmaceutically effective amount of a compound of formula II or III above.

As previously mentioned, the furan nitrone compounds of this invention have been found to be effective free radical spin traps. As such, these compounds are useful as analytical reagents for detecting free radicals. Additionally, the furan nitrones of this invention have been discovered to be useful as therapeutics for treating a wide variety of medical dysfunctions and diseases including, but not limited to, acute central nervous system (CNS) disorders, acute cardiovascular disorders, neurodegenerative conditions, inflammatory diseases and autoimmune conditions.

Accordingly, in one of its method aspects, this invention provides a method for treating a patient with an acute central nervous system disorder, said method comprising administering to said patient a pharmaceutical composition comprising a pharmaceutically acceptable carrier and an effective acute central nervous system disorder-treating amount of a compound of formula I above. In a preferred embodiment of this method, the acute central nervous system disorder treated is stroke.

In another of its method aspects, this invention provides a method for treating a patient with an acute cardiovascular disorder, said method comprising administering to said patient a pharmaceutical composition comprising a pharmaceutically acceptable carrier and an effective acute cardiovascular disorder-treating amount of a compound of formula I above. In a preferred embodiment of this method, the acute cardiovascular disorder treated is cardiac infarction.

In still another of its method aspects, this invention is directed to a method for treating a patient with a neurodegenerative disease which method comprises administering to said patient a pharmaceutical composition comprising a pharmaceutically acceptable carrier and an effective neurodegenerative disease-treating amount of a compound of formula I above. Additionally, this invention is directed to a method for preventing the onset of a neurodegenerative disease in a patient at risk for developing the neurodegenerative disease which method comprises administering to said patient a pharmaceutical composition comprising a pharmaceutically acceptable carrier and an effective neurodegenerative disease-preventing amount of a compound of formula I above.

In preferred embodiments of this invention, the neurodegenerative disease treated and/or prevented in the above methods is Alzheimer's disease, Parkinson's disease, HIV dementia and the like.

In yet another of its method aspects, this invention is directed to a method for treating a patient with an autoimmune disease which method comprises administering to said patient a pharmaceutical composition comprising a pharmaceutically acceptable carrier and an effective autoimmune disease-treating amount of a compound of formula I above. This invention is also directed to a method for preventing the onset of an autoimmune disease in a patient at risk for developing the autoimmune disease which method comprises administering to said patient a pharmaceutical composition comprising a pharmaceutically acceptable carrier and an effective autoimmune disease-preventing amount of a compound of formula I above.

In preferred embodiments of this invention, the autoimmune disease treated and/or prevented in the above methods is systemic lupus, multiple sclerosis and the like.

In still another of its method aspects, this invention is directed to a method for treating a patient with an inflammatory disease which method comprises administering to said patient a pharmaceutical composition comprising a pharmaceutically acceptable carrier and an effective inflammatory disease-treating amount of a compound of formula I above. Additionally, this invention is directed to a method for preventing the onset of an inflammatory disease in a patient at risk for developing the inflammatory disease which method comprises administering to said patient a pharmaceutical composition comprising a pharmaceutically acceptable carrier and an effective inflammatory disease-preventing amount of a compound of formula I above.

In preferred embodiments of this invention, the inflammatory disease treated and/or prevented in the above methods is rheumatoid arthritis, septic shock, erythema nodosum leprosy, septicemia, uveitis and the like.

This invention is also directed to processes for preparing the furan nitrone compounds of formula I. Accordingly, in one of its process aspects, this invention provides a process for preparing a compound of formula I:

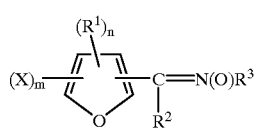

wherein each $R^1$ is independently selected from the group consisting of hydrogen, alkyl, substituted alkyl, alkenyl, alkynyl, alkaryl, aryl, alkoxy, alkcycloalkyl, cycloalkyl, cycloalkenyl and halo;

$R^2$ is selected from the group consisting of hydrogen, alkyl, substituted alkyl, alkenyl, alkynyl, alkaryl, aryl, alkcycloalkyl, cycloalkyl and cycloalkenyl;

$R^3$ is selected from the group consisting of alkyl, substituted alkyl, alkenyl, alkynyl, alkaryl, aryl, alkcycloalkyl, cycloalkyl and cycloalkenyl;

each X is independently selected from the group consisting of $-SO_3Y$, $-S(O)R^4$, $-SO_2R^5$ and $-SO_2NR^6R^7$;

wherein Y is hydrogen or a pharmaceutically acceptable cation;

$R^4$ is selected from the group consisting of alkyl, substituted alkyl, alkenyl, alkynyl, alkaryl, aryl, alkcycloalkyl, cycloalkyl and cycloalkenyl;

$R^5$ is selected from the group consisting of alkyl, substituted alkyl, alkenyl, alkynyl, alkaryl, aryl, alkcycloalkyl, cycloalkyl and cycloalkenyl;

$R^6$ and $R^7$ are independently selected from the group consisting of hydrogen, alkyl, substituted alkyl, alkenyl, alkynyl, alkaryl, aryl, alkcycloalkyl, cycloalkyl and cycloalkenyl; or $R^6$ and $R^7$ together with the nitrogen atom to which they are attached can form a heterocyclic ring containing from 2 to 8 carbon atoms and optionally from 1 to 3 additional heteroatoms selected from the group consisting of oxygen, nitrogen and sulfur;

m is an integer from 1 to 3; and n is an integer from 0 to 2, provided that m+n=3, said process comprising reacting a furan carbonyl compound of the formula:

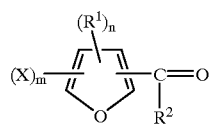

with a hydroxylamine of the formula:

to provide a compound of formula I.

In another of its process aspects, the present invention provides a process for preparing a sulfamoyl-substituted furan nitrone of formula I':

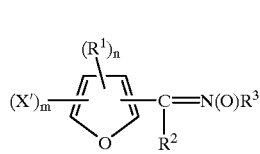

wherein each $R^1$ is independently selected from the group consisting of hydrogen, alkyl, substituted alkyl, alkenyl, alkynyl, alkaryl, aryl, alkoxy, alkcycloalkyl, cycloalkyl, cycloalkenyl and halo;

$R^2$ is selected from the group consisting of hydrogen, alkyl, substituted alkyl, alkenyl, alkynyl, alkaryl, aryl, alkcycloalkyl, cycloalkyl and cycloalkenyl;

$R^3$ is selected from the group consisting of alkyl, substituted alkyl, alkenyl, alkynyl, alkaryl, aryl, alkcycloalkyl, cycloalkyl and cycloalkenyl;

each X' is $-SO_2NR^6R^7$; wherein $R^6$ and $R^7$ are independently selected from the group consisting of hydrogen, alkyl, substituted alkyl, alkenyl, alkynyl, alkaryl, aryl, alkcycloalkyl, cycloalkyl and cycloalkenyl; or $R^6$ and $R^7$ together with the nitrogen atom to which they are attached can form a heterocyclic ring containing from 2 to 8 carbon atoms and optionally from 1 to 3 additional heteroatoms selected from the group consisting of oxygen, nitrogen and sulfur;

m is an integer from 1 to 3; and n is an integer from 0 to 2, provided that m+n3, said process comprising the steps of:

(a) reacting a carbonyl-substituted furan sulfonic acid compound of the formula:

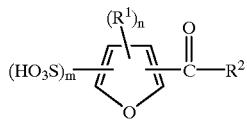

with phosphorous trichloride and phosphorous pentachloride to provide a gem-dichloride-substituted furan sulfonyl chloride compound of the formula:

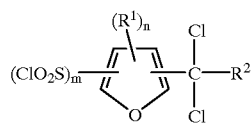

(b) reacting the gem-dichloride-substituted furan sulfonyl chloride compound with an amine of the formula:

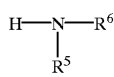

to provide a gem-dichloride-substituted furan sulfonamide compound of the formula:

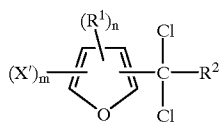

(c) hydrolyzing the gem-dichloride-substituted furan sulfonamide compound to provide a carbonyl-substituted furan sulfonamide compound of the formula:

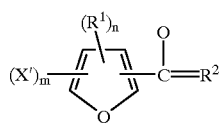

and;

(d) reacting the carbonyl-substituted furan sulfonamide with a hydroxylamine of the formula:

to provide a compound of formula I'.

In another of its aspects, this invention is directed to the use of a compound of formula I, II or III above in the manufacture of a formulation or medicament for a medicinal treatment. Preferably, the medical treatment is the therapeutic or prophylactic treatment of an acute central nervous system disorder, an acute cardiovascular disorder, a neurodegenerative disease, an autoimmune disease or an inflammatory disease.

BRIEF DESCRIPTION OF THE DRAWINGS

FIGS. 3A, 3B and 3C show the wanderings of rodents in a enclosed grid. Specifically, FIG. 3A shows the wandering of a rodent treated with a 1% methylcellulose/saline control. FIG. 3B shows the wandering of a rodent treated with 1% methylcellulose/nitroarginine. And FIG. 3C shows the wandering of a rodent treated with nitroarginine and 10 mg/kg of a furan nitrone of formula I (Compound 1).

DETAILED DESCRIPTION OF THE INVENTION

Figure 1:
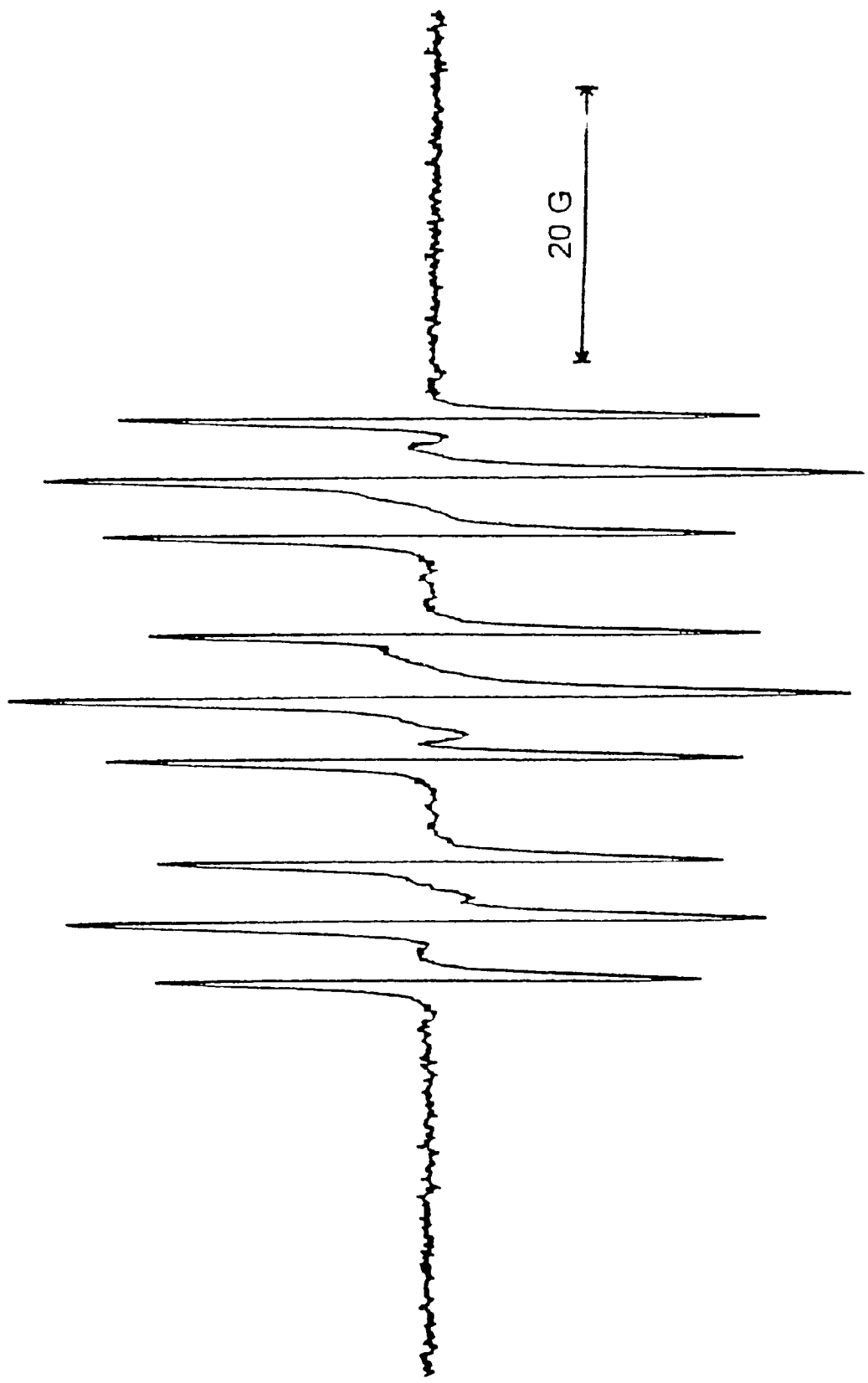
FIG. 1 is an electron spin resonance (ESR) spectra of the radical adduct of N-isopropyl-α-(2-sulfofuran-5-yl)nitrone sodium salt and a methyl radical.

As discussed above, the furan nitrone compounds of this invention are useful as free radical trapping agents. Accordingly, such compounds are useful as analytical reagents for detecting free radicals. Additionally, the furan nitrones of this invention have been discovered to be useful as therapeutics for treating a wide variety of medical dysfunctions and diseases.

In the furan nitrone compounds of formula I, the substituents may be located at any of the carbon atoms of the furan ring. The furan ring positions are specified herein using conventional furan nomenclature, i.e., the furan ring oxygen is the 1 position; the two carbon atoms immediately adjacent the ring oxygen are designated the 2 and 5 positions; and the remaining two carbons are designated the 3 and 4 positions. Thus, a representative compound of formula I having a single sulfonate group at the 2 position and an isopropyl nitrone at the 5 position would be named N-isopropyl-α-(2-sulfofuran-5-yl)nitrone.

Definitions

The term "β-amyloid peptide" refers to a 39–43 amino acid peptide having a molecular weight of about 4.2 kD, which peptide is substantially homologous to the form of the protein described by Glenner, et al., *Biochem. Biophys. Res. Commun.*, 120:885–890 (1984), including mutations and post-translational modifications of the normal β-amyloid peptide.

The term "cytokines" refers to peptide protein mediators that are produced by immune cells to modulate cellular functions. Examples of cytokines include, interleukin-1β (IL-1β), interleukin-6 (IL-6) and tumor necrosis factor-α (TNFα).

"Alkyl" refers to monovalent alkyl groups preferably having from 1 to about 12 carbon atoms, more preferably 1 to 8 carbon atoms and still more preferably 1 to 6 carbon atoms. This term is exemplified by groups such as methyl, ethyl, n-propyl, isopropyl, n-butyl, isobutyl, tert-butyl, n-hexyl, n-octyl, tert-octyl and the like. The term "lower alkyl" refers to alkyl groups having 1 to 6 carbon atoms.

"Substituted alkyl" refers to an alkyl group preferably having from 1 to about 12 carbon atoms, more preferably 1 to 8 carbon atoms and still more preferably 1 to 6 carbon atoms, which is substituted with from 1 to 3 substituents selected from the group consisting of alkoxy, amino, mono- and dialkylamino, aminoacyl, aminocarbonyl, alkoxycarbonyl, aryl, carboxyl, cyano, halo, heterocyclic, hydroxy, nitro, thioalkoxy and the like. A preferred substituted alkyl group is the trifluoromethyl group.

"Alkylene" refers to divalent alkylene groups preferably having from 1 to 10 carbon atoms and more preferably 1 to 6 carbon atoms which can be straight chain or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Alkenylene" refers to divalent alkenylene groups preferably having from 2 to 10 carbon atoms and more preferably 2 to 6 carbon atoms which can be straight chain or branched and having at least 1 and preferably from 1–2 sites of alkenyl unsaturation. This term is exemplified by groups such as ethenylene (—CH═CH—), the propenylene isomers (e.g., —CH═CHCH$_2$— and —C(CH$_3$)═CH— and —CH═C(CH$_3$)—) and the like.

"Alkaryl" refers to -alkylene-aryl groups preferably having from 1 to 10 carbon atoms in the alkylene moiety and from 6 to 14 carbon atoms in the aryl moiety. Such alkaryl groups are exemplified by benzyl, phenethyl, and the like.

"Alkcycloalkyl" refers to -alkylene-cycloalkyl groups preferably having from 1 to 10 carbon atoms in the alkylene moiety and from 3 to 8 carbon atoms in the cycloalkyl moiety. Such alkcycloalkyl groups are exemplified by —CH$_2$-cyclopropyl, —CH$_2$-cyclopentyl, —CH$_2$CH$_2$-cyclohexyl, and the like.

"Alkoxy" refers to the group "alkyl-O—". Preferred alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Alkoxycarbonyl" refers to the group —C(O)OR where R is alkyl.

"Alkenyl" refers to alkenyl groups preferably having from 2 to 10 carbon atoms and more preferably 2 to 6 carbon atoms and having at least 1 and preferably from 1–2 sites of alkenyl unsaturation. Preferred alkenyl groups include ethenyl (—CH═CH$_2$), n-propenyl (—CH$_2$CH═CH$_2$), isopropenyl (—C(CH$_3$)═CH$_2$), and the like.

"Alkynyl" refers to alkynyl groups preferably having from 2 to 10 carbon atoms and more preferably 2 to 6 carbon atoms and having at least 1 and preferably from 1–2 sites of allynyl unsaturation. Preferred allynyl groups include ethynyl (—C≡CH), propargyl (—CH$_2$C≡CH), and the like.

"Aminocarbonyl" refers to the group —C(O)NRR where each R is independently hydrogen or alkyl.

"Aminoacyl" refers to the group —NRC(O)R where each R is independently hydrogen or alkyl.

"Aryl" refers to an unsaturated aromatic carbocyclic group of from 6 to 14 carbon atoms having a single ring (e.g., phenyl) or multiple condensed rings (e.g., naphthyl or anthryl). Preferred aryls include phenyl, naphthyl and the like. Unless otherwise constrained by the definition for the individual substituent, such aryl groups can optionally be substituted with from 1 to 3 substituents selected from the group consisting of alkyl, substituted alkyl, alkoxy, alkenyl, alkynyl, amino, aminoacyl, aminocarbonyl, alkoxycarbonyl, aryl, carboxyl, cyano, halo, hydroxy, nitro, trihalomethyl and the like.

"Cycloalkyl" refers to cyclic alkyl groups of from 3 to 10 carbon atoms having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantanyl, and the like.

"Cycloalkenyl" refers to cyclic alkenyl groups of from 4 to 10 carbon atoms having a single cyclic ring and at least one point of internal unsaturation which can be optionally substituted with from 1 to 3 alkyl groups. Examples of suitable cycloalkenyl groups include, for instance, cyclopent-3-enyl, cyclohex-2-enyl, cyclooct-3-enyl and the like.

"Halo" or "halogen" refers to fluoro, chloro, bromo and iodo. Preferred halo groups are either fluoro or chloro.

"Heterocycle" or "heterocyclic" refers to a monovalent saturated or unsaturated group having a single ring or multiple condensed rings, from 1 to 10 carbon atoms and from 1 to 4 hetero atoms selected from nitrogen, sulfur or oxygen within the ring. Examples of heterocycles include, but are not limited to, morpholine, piperazine, imidazolidine, pyrrolidine, piperidine and the like.

"Pharmaceutically acceptable salt" refers to pharmaceutically acceptable salts which are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate and the like. The term "pharmaceutically acceptable cation" refers to a pharmaceutically acceptable cationic counterion of an acidic functional group. Such cations are exemplified by sodium, potassium, calcium, magnesium, ammonium, tetraakylammonium cations, and the like. Pharmaceutically acceptable salts of the furan nitrones of this invention are prepared using conventional procedures well known to those skilled in the art including, for example, treating a sulfonic acid derivative with an appropriate base.

"Thioalkoxy" refers to the group "alkyl-S—". Preferred thioalkoxy groups include, by way of example, thiomethoxy, thioethoxy, n-thiopropoxy, isothiopropoxy, n-thiobutoxy and the like.

General Synthetic Procedures

The furan nitrone compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protecting and deprotecting various functional groups are well known in the art. For example, numerous protecting groups, and their introduction and removal, are described in T. W. Greene and G. M. Wuts, *Protecting Groups in Organic Synthesis,* Second Edition, Wiley, New York, 1991, and references cited therein.

In a preferred method of synthesis, the furan nitrone compounds of this invention are prepared by coupling a furan carbonyl compound of formula IV:

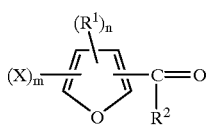

wherein $R^1$, $R^2$, X, m and n are as defined above, with a hydroxylamine of formula V:

$$HO—NH—R^3 \quad\quad V$$

wherein $R^3$ is as defined above, under conventional reaction conditions.

The coupling reaction is typically conducted by contacting the furan carbonyl compound IV with at least one equivalent, preferably about 1.1 to about 2 equivalents, of hydroxylamine V in an inert polar solvent such as methanol, ethanol, 1,4-dioxane, tetrahydrofuran, dimethylsulfoxide, dimethylformamide and the like. This reaction is preferably conducted at a temperature of from about 0° C. to about 100° C. for about 1 to about 48 hours. Optionally, a catalytic amount of an acid, such as acetic acid, p-toluenesulfonic acid and the like, may be employed in this reaction. Upon completion of the reaction, the furan nitrone of formula I is recovered by conventional methods including precipitation, chromatography, filtration, distillation and the like.

The furan carbonyl compounds of formula IV employed in the coupling reaction are either known compounds or can be prepared from known compounds by conventional procedures. Preferred furan carbonyl compounds include, but are not limited to, 5-formylfuran-2-sulfonic acid, 4formylfuran-2-sulfonic acid, 3-formylfuran-2-sulfonic acid, 2-formylfuran-3-sulfonic acid, 4-formylfuran-3-sulfonic acid, 2-formylfuran-4-sulfonic acid, 5-acetylfuran-2-sulfonic acid, 4-acetylfuran-2-sulfonic acid, and the like. An especially preferred furan carbonyl compound is 5-formylfuran-2-sulfonic acid.

Particularly preferred furan carbonyl compounds for use in this invention are those compounds of formula IV wherein X is —SO$_3$Y and Y is as defined above. These compounds can be readily prepared by sulfonating furan carbonyl compounds of formula VI:

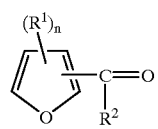

wherein $R^1$, $R^2$ and n are as defined above, using reagents and conditions well known to those skilled in the art. Any conventional sulfonating reagent, such as sulfur trioxide pyridine complex, may be used in this reaction. Typically, the sulfonation reaction is conducted by contacting a furan carbonyl compound of formula VI with about 1 to about 5 molar equivalent of the sulfonating reagent in an inert solvent, such as 1,2-dichloroethane, at a temperature ranging from about 50° C. to about 200° C., preferably at about 100° C to about 150° C., for about 6 to about 48 hours. Upon completion of the reaction, the sulfonated furan carbonyl compound is recovered by conventional methods including precipitation, chromatography, filtration and the like.

When a sulfonated furan carbonyl compound is employed in the coupling reaction with hydroxylamine V, the sulfonate group is preferably converted into a suitable salt, such as the lithium, sodium or potassium salt, prior to contacting the hydroxylamine with the furan carbonyl compound. The sulfonate group is readily converted into the corresponding salt by contacting the sulfonate with at least one equivalent of a suitable base, such as lithium hydroxide, sodium hydroxide, potassium hydroxide, sodium hydride and the like.

Another preferred group of furan carbonyl compounds for use in this invention are those compounds of formula IV wherein one or more X is —SO$_2$NR$^6$R$^7$ wherein $R^6$ and $R^7$ are as defined above. These compounds can be readily prepared from the corresponding sulfonated furan carbonyl compound, i.e., compounds of formula IV wherein X is —SO$_3$H, by converting the sulfonate group into a sulfonyl chloride and then coupling the sulfonyl halide with an amine of formula VII:

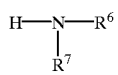

wherein $R^6$ and $R^7$ are as defined above. The amines of formula VII are either known compounds or compounds that can be prepared by known procedures. Examples of suitable amines for use in this reaction include, but are not limited to, ammonia, N-methylamine, N-ethylamine, N-n-propylamine, N-isopropylamine, N-n-butylamine, N-isobutylamine, N-sec-butylamine, N-tert-butylamine, N-n-pentylamine, N-cyclopentylamine, N-n-hexylamine, N-cyclohexylamine, N-n-octylamine, N-tert-octylamine, N,N-dimethylamine, N,N-diethylamine, N,N-di-n-propylamine, N,N-diisopropylamine, N,N-di-n-butylamine, N,N-diisobutylamine, N,N-di-sec-butylamine, N,N-di-n-hexylamine, N-methyl-N-ethylamine, N-methyl-N-n-propylamine, N-methyl-N-isopropylamine, N-methyl-N-n-butylamine, N-methyl-N-tert-butylamine, N-methyl-N-tert-octylamine, N-methyl-N-cyclopentylamine, N-methyl-N-cyclohexylamine, N-ethyl-N-n-propylamine, N-ethyl-N-isopropylamine, N-ethyl-N-n-butylamine, N-ethyl-N-cyclohexylamine, N-phenylamine, N-(4-methyl)phenylamine, pyrrolidine, piperidine, morpholine and the like.

The sulfonic acid, i.e., where X in formula IV is —SO$_3$H, can be converted into the corresponding sulfonyl chloride using phosphorous trichloride and phosphorous pentachloride. In addition to converting the sulfonic acid group(s) into the corresponding sulfonyl chloride, this reaction also converts the carbonyl group of compound IV into a gem-dichloride group. This transformation serves to protect the carbonyl group during subsequent sulfonamide formation.

Generally, the reaction of compound IV with PCl$_3$/PCl$_5$ is conducted using about 2 to 5 molar equivalents of phosphorous trichloride and phosphorous pentachloride, either neat or in an inert solvent, such as dichloromethane, at temperature in the range of about 0° C. to about 80° C. for about 1 to about 48 hours.

The sulfonyl chloride is then contacted with about 1 to about 5 molar equivalents of amine VII to afford the corresponding sulfonamide gem-dichloride compound. This reaction is preferably conducted at a temperature ranging from about –70° C. to about 40° C. for about 1 to about 24 hours. Typically, this reaction is conducted in the presence of a suitable base to scavenge the acid generated during the reaction. Suitable bases include, by way of example, triethylamine, diisopropylethylamine, N-methylmorpholine and the like. Alternatively, an excess of amine VII may be used to scavenge the acid generated during the reaction.

The gem-dichloride group is then hydrolyzed to regenerate the carbonyl group. This reaction is preferably conducted by contacting the sulfonamide gem-dichloride compound with an aqueous solution of formic acid (preferably about 75%) at a temperature ranging from about 50° C. to about 150° C. for about 1 to 24 hours. Upon completion of the reaction, the resulting sulfonamide furan carbonyl compound is recovered by conventional methods including precipitation, chromatography, filtration, and the like.

Another preferred group of furan carbonyl compounds for use in this invention are those compounds of formula IV wherein one or more X is —S(O)R$^4$ or —SO$_2$R$^5$ wherein R$^4$ and R$^5$ are as defined above. These compounds can be readily prepared from the corresponding sulfanyl furan carbonyl compound, i.e. wherein X in formula IV is —SR$^4$ or SR$^5$, by oxidation using conventional reagents and reaction conditions. Suitable reagents for oxidizing a sulfide compound to a sulfoxide include, by way of example, hydrogen peroxide, 3-chloroperoxybenzoic acid (MCPBA), sodium periodate and the like. Depending on the oxidizing agent employed, the carbonyl group of the furan intermediate is preferably protected as, for example, an acetal or a ketal, to prevent undesired oxidation.

The oxidation reaction is typically conducted by contacting the sulfanyl furan carbonyl compound with about 0.95 to about 1.1 equivalents of the oxidizing reagent in an inert diluent, such as dichloromethane, at a temperature ranging from about −50° C. to about 75° C. for about 1 to about 24 hours. The resulting sulfoxide can then be further oxidized to the corresponding sulfone by contacting the sulfoxide with at least one additional equivalent of an oxidizing reagent, such as hydrogen peroxide, MCPBA, potassium permanganate and the like. Alternatively, the sulfone can be prepared directly by contacting the sulfide with at least two equivalent, and preferably an excess, of the oxidizing reagent. If desired, these oxidation reactions can also be conducted after coupling the furan carbonyl compound of formula IV with the hydroxylamine V.

Alternatively, the sulfone compounds of formula IV wherein one or more X is —SO$_2$R$^5$ where R$^5$ is as defined above, can be prepared by reacting the corresponding bromo furan carbonyl compound with, for example, a sulfinic acid sodium salt (i.e., a compound of the formula R$^5$—SO2Na, wherein R$^5$ is as defined above). This reaction is typically conducted by contacting the bromofuran carbonyl compounds with an excess, preferably 1.2 to 3 equivalents, of the sulfinic acid in an inert solvent, such as 2-ethoxyethanol, at a temperature ranging from about 50° C. to about 150° C. for about 2 to 24 hours. The resulting sulfone furan carbonyl compound can then be coupled with a hydroxylamine compound of formula V using conventional reaction conditions.

The hydroxylamine compounds of formula V above are also known compounds or compounds which can be prepared from known compounds by conventional procedures. Typically, the hydroxylamine compounds of formula V are prepared by reduction of the corresponding nitro compound (i.e., R$^3$—NO$_2$, wherein R$^3$ is as defined above) using a suitable catalyst such as an activated zinc/acetic acid catalyst or an aluminum/mercury amalgam catalyst. This reaction is typically conducted at a temperature ranging from about 15° C. to about 100° C. for about 0.5 to 12 hours, preferably about 2 to 6 hours, in an aqueous reaction media, such as an alcohol/water mixture in the case of the zinc catalyst or an ether/water mixture in the case of the aluminum amalgam catalyst. Hydroxylamines can also be prepared by reduction of oximes with hydride reducing agents, such as sodium cyanoborohydride. Aliphatic nitro compounds (in the form of their salts) can also be reduced to hydroxylamines using borane in tetrahydrofuran. Since some hydroxylamines have limited stability, such compounds are generally prepared immediately prior to reaction with the furan carbonyl compound of formula IV. Alternatively, hydroxylamines can often be stored (or purchased commercially) as their hydrochloride salts. In such cases, the free hydroxylamine is typically generated immediately prior to reaction with the furan carbonyl compound by reaction of the hydrochloride salt with a suitable base, such as sodium hydroxide, sodium methoxide and the like.

Preferred hydroxylamines for use in this invention include, but are not limited to, N-methylhydroxylamine, N-ethylhydroxylamine, N-n-propylhydroxylamine, N-isopropylhydroxylamine, N-n-butylhydroxylamine, N-isobutylhydroxylamine, N-sec-butylhydroxylamine, N-tert-butylhydroxylamine, N-n-pentylhydroxylamine, N-cyclopentylhydroxylamine, N-n-hexylhydroxylamine, N-cyclohexylhydroxylamine, N-n-octylhydroxylamine, N-tert-octylhydroxylamine, N-phenylhydroxylamine and the like.

In some cases, the furan nitrones of this invention will contain one or more chiral centers. Typically, such compounds will be prepared as a racemic mixture. If desired, however, such compounds can be prepared or isolated as pure stereoisomers, i.e., as individual enantiomers or diastereomers, or as stereoisomer-enriched mixtures. All such stereoisomers (and enriched mixtures) of the furan nitrones of formula I are included within the scope of this invention. Pure stereoisomers (or enriched mixtures) may be prepared using, for example, optically active starting materials or stereoselective reagents well known in the art. Alternatively, racemic mixtures of such compounds can be separated using, for example, chiral column chromatography, chiral resolving agents and the like.

Pharmaceutical Compositions

When employed as pharmaceuticals, the furan nitrone compounds of this invention are typically administered in the form of a pharmaceutical composition comprising at least one active furan nitrone compound and a carrier or vehicle suitable for use in pharmaceutical compositions, i.e., a pharmaceutically acceptable carrier. Such carriers are well known in the pharmaceutical art as are procedures for preparing pharmaceutical compositions.

Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of this invention can be administered by a variety of routes including oral, rectal, transdermal, subcutaneous, intravenous, intramuscular, and intranasal. Depending on the intended route of delivery, the compounds of this invention are preferably formulated as either injectable or oral compositions.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furan nitrone compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the furan nitrone compound in such compositions is typically a minor component, often being from about 0.05 to 10% by weight with the remainder being the injectable carrier and the like.

The above described components for orally administrable or injectable compositions are merely representative. Other materials as well as processing techniques and the like are set forth in Part 8 of *Remington's Pharmaceutical Sciences*, 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in the incorporated materials in *Remington's Pharmaceutical Sciences*.

The following formulation examples illustrate representative pharmaceutical compositions of this invention. The present invention, however, is not limited to the following exemplified pharmaceutical compositions.

Formulation 1 - Tablets

A compound of formula I is admixed as a dry powder with a dry gelatin binder in an approximate 1:2 weight ratio. A minor amount of magnesium stearate is added as a lubricant. The mixture is formed into 240–270 mg tablets (80–90 mg of active furan nitrone compound per tablet) in a tablet press.

Formulation 2 - Capsules

A compound of formula I is admixed as a dry powder with a starch diluent in an approximate 1:1 weight ratio. The mixture is filled into 250 mg capsules (125 mg of active furan nitrone compound per capsule).

Formulation 3 - Liquid

A compound of formula I (50 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4 - Tablets

The compound of formula I is admixed as a dry powder with a dry gelatin binder in an approximate 1:2 weight ratio. A minor amount of magnesium stearate is added as a lubricant. The mixture is formed into 450–900 mg tablets (150–300 mg of active furan nitrone compound) in a tablet press.

Formulation 5 - Injection

The compound of formula I is dissolved in a buffered sterile saline injectable aqueous medium to a concentration of approximately 5 mg/ml.

Compound Utility

The furan nitrone compounds of this invention have been discovered to effectively trap or scavenge free radicals and, accordingly, such compounds are useful as analytical reagents for detecting free radicals using, for example, ESR spectroscopy techniques. Additionally, the furan nitrones of this invention have been discovered to be useful for treating a wide variety of medical dysfunctions and diseases.

As analytical reagents, the furan nitrone compounds of this invention are useful as spin traps for detecting unstable free radicals using electron spin resonance (ESR) spectroscopy and related techniques. When used as analytical reagents, the furan nitrone compounds of this invention are typically contacted with the radical to be studied in solution and an ESR spectrum generated in a conventional manner. Any ESR spectrometer, such as a JEOL JES-FE3XG spectrometer, may be employed in these experiments. Typically, the solution containing the spin-trap will be deoxygenated by, for example, bubbling argon or nitrogen through the solution before the ESR experiment is conducted. Preferably, an excess of the furan nitrone is used in such ESR experiments.

The actual experimental procedures employed in the spin-trapping experiment will depend on a number of factors, such as the manner of radical production, the inertness of the solvent and reagents with respect to the spin trap, the lifetime of the spin adduct and the like. Spin trapping procedures are well known in the art and the exact procedure employed can be determined by those skilled in the art. Typical procedures and apparatus for conducting spin trapping experiments are described, for example, in C. A. Evans, "Spin Trapping", *Aldrichimica Acta*, (1979), 12(2), 23–29, and references cited therein.

As therapeutics, the furan nitrones of this invention have been found to be useful for treating a wide variety of medical dysfunctions and diseases. While not wishing to be limited to theory, it is believed that one mode of action for the furan nitrone compounds of this invention is the trapping or scavenging of free radicals. Accordingly, the furan nitrones of formula I are useful for treating medical dysfunctions or diseases arising from or characterized by free radical-induced oxidative damage.

Such medical dysfunctions or diseases include, by way of example, disorders of the central nervous system, such as stroke, aging, Parkinsonism, multiple sclerosis, concussion, aneurysm, ventricular hemorrhage and associated vasospasm, migraine and other vascular headaches, spinal cord trauma, diabetic retinopathy, neuroanesthesia adjunct, and dementia including age-related dementia, Alzheimer's disease, multi-infarct dementia, HIV dementia and Parkinsonian dementia; disorders of the peripheral nervous system, such as diabetic peripheral neuropathy and traumatic nerve damage; and disorders of the peripheral organs, such as atherosclerosis (both diabetic and spontaneous), cardiac infarction, chronic obstructive pulmonary disease (COPD), pancreatitis, uveitis, pulmonary fibrosis due to chemotherapeutic agents, angioplasty, trauma, burns, ischemic bowel disease, wounds, ulcers and bed sores, lupus, ulcerative colitis, organ transplantation, renal hypertension, overexertion of skeletal muscle, and epistaxis (pulmonary bleeding). Other conditions that can be treated include inflammatory diseases, such as arthritis; undesirable or altered oxidation of low density lipoprotein; and dysfunctions from exposure to radiation, including X-ray, ultraviolet, gamma and beta radiation, and cytotoxic compounds, including those used for chemotherapy for cancer and viral infections. Antioxidants may also provide protective effects against cancers and inhibit cell proliferation. See, for example, K. Irani et al., *Science*, 275:1649–1652 (1997).

Additionally, the furan nitrones of this invention have been discovered to effectively inhibit the release of cytokines, such a IL-1β, IL-6 and TNFα. Elevated levels of cytokines are associated with a wide variety of inflammatory neurodegenerative and autoimmune conditions, including Alzheimer's disease, AIDS dementia, septic shock, rheumatoid arthritis, erythema nodosum leprosy, meningococcal meningitis, multiple sclerosis, systemic lupus and the like. See, L. Sekut et al., *Drug News Perspect.* 1996, 9, 261; K. Shiosaki et al., "Chapter 4. Emerging Opportunities in Neuroinflammatory Mechanisms of Neurodegeneration" *Annual Reports in Medicinal Chemistry*, pp. 31–40, Academic Press (1995) and reference cited therein; and A. Waage et al., *J. Exp. Med.* 1989, 170, 1859–1867. Accordingly, the furan nitrones of formula I are useful for treating diseases characterized by an overproduction or an unregulated production of cytokines, particularly IL-1β, IL-6 and TNFα, including neurodegenerative, autoimmune and/or inflammatory conditions.

Moreover, the furan nitrones have been found to effectively inhibit the formation of Aβ(1–40) beta-pleated sheets and/or protect against neuronal cell loss. Additionally, in in vivo tests, such compounds have been found to reduce the locomotor impairment caused by Aβ(25–35). The formation of Aβ(1–40) beta-pleated sheets, neuronal cell loss, and beta amyloid-induced locomotor impairment have been associated with neurodegenerative conditions, such as Alzheimer's disease, and/or autoimmune conditions. Accordingly, the furan nitrones of formula I are useful for preventing and/or treating neurodegenerative and/or autoimmune conditions.

Among the various medical conditions which may be prevented and/or treated, the furan nitrones of this invention are particularly useful for treating conditions involving acute intense oxidative damage to a region of the central nervous system. Examples of such conditions include stroke, conditions associated with stroke, concussion and subarachnoid hemorrhage. When treating such conditions, the furan nitrone compound will typically be administered in a manner that allows the compound to enter the patient's bloodstream as quickly and directly as possible. Typically, this involves intravenous administration.

Intravenous dose levels for treating these medical conditions range from about 0.1 mg/kg/hour to at least 10 mg/kg/hour over a period of from about 1 to about 120 hours and especially 24 to 96 hours. Preferably, an amount of at least about 0.2 mg/kg/hour is administered to the patient. A preloading bolus of from about 10 mg to about 500 mg may also be administered to achieve adequate steady state levels.

While intravenous administration is preferred, other forms of parenteral administration, such as intramuscular injection can be used, as well. In such cases, dose levels similar to those described above may be employed.

Among other factors, a surprising and unexpected advantage of the furan nitrones of this invention is that such compounds can be administered at vastly higher levels than are possible with certain other known free radical traps, such as N-tert-butyl-α-phenylnitrone (PBN). Doses of up to 300 mg/kg/hour and higher or intravenous bolus doses of from 10 to 1000 mg/kg may be employed using the compounds of this invention. In contrast, PBN causes death or acute toxicity at high dosages. Accordingly, large doses of a furan nitrone compound may be administered immediately post stroke or other trauma to provide significantly reduced oxidative damage in many cases. Such dosages, and the accompanying benefits, are not possible using PBN.

Another acute condition which can be advantageously treated with the furan nitrones of this invention is acute oxidative damage to the cardiovascular system, such as the damage which occurs in a patient who has suffered a cardiac infarction or the like. When treating such a condition, a pharmaceutical composition comprising a furan nitrone is administered parenterally, e.g. intravenously, at doses similar to those described above for stroke and other acute CNS conditions.

Other medical conditions which may be prevented and/or treated with the furan nitrone compounds of this invention are neurodegenerative conditions, such as Alzheimer's disease, Parkinson's disease, HIV-dementia and the like; autoimmune conditions, such as systemic lupus (erythematosus), multiple sclerosis and the like; and inflammatory conditions, such as inflammatory bowel disease, rheumatoid arthritis, septic shock, erythema nodosum leprosy, septicemia, uveitis, and the like. With regard to these disease classifications, it will be appreciated by those skilled in the art, that some disease conditions may be classified as, for example, both autoimmune and inflammatory conditions, such as multiple sclerosis and the like.

As discussed above, the compounds described herein are suitable for use in a variety of drug delivery systems. Injection dose levels for treating neurodegenerative, autoimmune and inflammatory conditions range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as neurodegenerative and autoimmune conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.02 to about 50 mg/kg of furan nitrone, with preferred doses each providing from about 0.04 to about 30 mg/kg and especially about 1 to about 10 mg/kg.

When used to prevent the onset of a neurodegenerative, autoimmune or inflammatory condition, the furan nitrone compounds of this invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition. When used prophylactically, a pharmaceutical composition comprising a furan nitrone is administered orally to the predisposed patient The doses for this oral therapy will typically be the same as those set forth above for treating persons suffering from the neurodegenerative, autoimmune or inflammatory condition.

The compounds of this invention can be administered as the sole active agent or they can be administered in combination with other agents, including other active furan nitrone compounds.

The following synthetic and biological examples are offered to illustrate this invention and are not to be construed in any way as limiting the scope of this invention.

EXAMPLES

In the examples below, the following abbreviations have the following meanings. Abbreviations not defined below have their generally accepted meaning.
bd=broad doublet
bs=broad singlet
d=doublet
dd=doublet of doublets
DCF=dichlorofluorescein
dec=decomposed
$dH_2O$=distilled water
ELISA=enzyme-linked immuno-sorbent assay
EtOAc=ethyl acetate
EtOH=ethanol
FBS=fetal bovine serum
g=grams
h=hours
Hz=hertz
IL-1β=interleukin-1β
IL-6=interleukin6
L=liter
LPS=lipopolysaccharide
m=multiplet
min=minutes
M=molar
MEM=minimum essential medium (or modified Eagle's medium
MeOH=methanol
mg=milligram
MHz=megahertz
mL=milliliter
mmol=millimole
m.p.=melting point
N=normal
q=quartet
quint.=quintet
ROS=reactive oxygen species
s=singlet
t=triplet
tert-octyl=1,1,3,3-tetramethylbutyl
THF=tetrahydrofuran
ThT=thioflavin T
tlc=thin layer chromatography
TNFα=tumor necrosis factor-α
μg=microgram
μL=microliter
UV=ultraviolet In the examples below, all temperatures are in degrees Celsius (unless otherwise indicated). Examples A–C below describe the synthesis of an intermediate used to prepare the furan nitrone compounds of this invention; Examples 1–17 describe the synthesis of furan nitrone compounds; and Examples 18–29 describe the in vitro and in vivo testing of such compounds.

Example A

Synthesis of N-Isopropylhydroxylamine

Acetic acid (10.8 g) was added to a cooled solution of 2-nitropropane (5.35 g) and zinc dust (5.89 g) in 95% ethanol (350 mL) at such a rate to maintain the temperature below 10° C. The reaction was stirred for three hours and the solvent removed in vacuo. The residue was extracted three times with dichloromethane. The combined extracts were dried over magnesium sulfate, filtered, and solvent stripped. The crude hydroxylamine product was used without further purification. Other hydroxylamines may also be prepared by this procedure.

Example B

Synthesis of Hydroxylamines By Reduction of Oximes

Various hydroxylamines were prepared according to the procedures of R. F. Borch et al., *J. Amer. Chem. Soc.*, 1971, 93(3):2897 from the corresponding oxime. Specifically, a 3-necked round bottom flask equipped with a stirring motor, a pH meter probe and an addition funnel is charged with a solution of the oxime in methanol (ca. 0.4 M). To the stirring solution is added 0.68 equivalents of $NaBH_3CN$ in portions. The addition funnel is filled with 4M HCl in MeOH. The amount of the acid solution prepared should be roughly ¾ of the volume of MeOH used to dissolve the oxime. The HCl solution is then added slowly to the oxime until pH comes down to about 4 and stabilizes at that value. The solution is then allowed to stir at ambient temperature for ca. 4 hours. HCl is added as necessary to keep the pH at 4. (A small sample can be periodically removed and worked-up to determine if the reaction is complete). When the reaction is complete, the solution is decanted into a 1-necked round bottom flask and MeOH is removed in vacua. (While removing the methanol by rotoevaporation, the solvent trap should be filled with NaOH (1 eq.) to quench HCN stripped off with MeOH). After the methanol has been removed, the residue is dissolved in water and extracted with methylene chloride (4x). The organic phases are combined, dried over $MgSO_4$ and stripped to dryness to provide the hydroxylamine product (as determined by NMR and DSC).

Example C

Synthesis of N-Cyclohexylhydroxylamine

N-Cyclohexylhydroxylamine hydrochloride (commercially available from Aldrich, 1001 West Saint Paul Avenue, Milwaukee, Wis. 53233 U.S.A.) was suspended in ether (about 200 mL of ether for 6 grams of the hydroxylamine salt) and extracted three times with 5% NaOH in brine. The organic phase (white fluffy crystals of N-cyclohexylhydroxylamine suspended in ether) was transferred to a round bottom flask and the ether was removed in vacuo. The resulting crystals were dried under a high vacuum for about 20 min. to afford the title compound.

Example 1

Synthesis of N-Isopropyl-α-(2sulfofuran-5-yl) nitrone

N-Isopropylhydroxylamine (from Example A above) and 5-formylfuran-2-sulfonic acid, sodium salt hydrate (5.94 g) were refluxed in methanol (200 mL) for 24 hours. Another portion of N-isopropylhydroxylamine was added and the reaction stirred for 24 hours. The solvent was stripped to provide a pale yellow solid which was recrystallized from ethyl acetate to afford 5.72 g (75% yield) of the title compound, m.p.=230° C. (decomposed). HPLC analysis showed a major product of 88% by area. Depending upon the pH, the title compound was present as the free acid, or, if in the presence of sodium cations and a higher pH, as the sodium salt. Other salt forms can be prepared by changing the cation.

Spectroscopic data was as follows:

IR (KBr, cm$^{-1}$): 2984.5 (CH), 2940 (CH), 1637.0 (C=N), 1216.1 (SO$_3$) and 1049.7 (N—O).

$^1$H NMR (DMSO-d$_6$, 270 MHz): δ=8.03 (1H, s, nitronyl H), 7.41 (1H, d, J=3.5 Hz, 4-aryl H), 6.49 (1H, d, J=3.3 Hz, 3-aryl H), 4.32 (1H, m, J=6.5 Hz; C—H), 1.27 (6H, d, J=6.5 Hz, CH$_3$).

$^{13}$C NMR (DMSO-d$_6$, 270 MHz): δ=158.20, 147.03, 122.96, 113.89, 110.23, 65.23 and 20.63.

Example 2

Synthesis of N-Propyl-α-(2-sulfofuran-5-yl)nitrone

Following the procedure of Example 1 above and using 5-formylfuran-2-sulfonic acid, sodium salt hydrate and N-propylhydroxylamine, the title compound was prepared in 41% yield as the sodium salt, m.p. 230–233° C. (dec.).

Spectroscopic data was as follows:

$^1$H NMR (DMSO-d$_6$, 90 MHz): δ=8.047 (1H, s, nitronyl CH), 7.459 (1H, d, J=3.4 Hz, furan CH), 6.524 (1H, d, J=3.4 Hz, furan CH), 3.865 (2H, t, J=6.7 Hz, CH$_2$), 1.805 (2H, m, CH$_2$), and 0.862 (3H, t, 7.3 Hz, CH$_3$).

Example 3

Synthesis of N-n-Butyl-α-(2-sulfofuran-5-yl)nitrone

Following the procedure of Example 1 above and using 5-formylfuran-2-sulfonic acid, sodium salt hydrate and N-n-butylhydroxylamine, the title compound was prepared in 6.7% yield as the sodium salt, m.p. 212.8° C. (dec).

Spectroscopic data was as follows:

IR (KBr, cm$^{-1}$): 2959.2 (CH), 2931.9 (CH), 1636 (C=N), 1246 (SO$_3$), 1225.2 (SO$_3$) and 1165.4 (N—O).

$^1$H NMR (DMSO-d$_6$, 270 MHz): δ=8.139 (1H, s, nitronyl CH), 7.677 (1H, d, J=3.7 Hz, furan CH), 7.047 (1H, d, J=3.7 Hz, furan CH), 4.026 (2H, t, J=6.9 Hz, CH$_2$), 1.889 (2H, m, CH$_2$), 1.373 (2H, m, CH$_2$) and 0.950 (3H, t, J=7.4 Hz, CH$_3$).

$^{13}$C NMR (DMSO-d$_6$, 270 MHz): δ=153.699, 146.774, 130.713, 118.037, 113.766, 64.742, 28.561, 18.540 and 12.438.

Example 4

Synthesis of N-tert-Butyl-α-(2-sulfofuran-5-yl) nitrone

Following the procedure of Example 1 above and using 5-formylfuran-2-sulfonic acid, sodium salt hydrate and N-tert-butylhydroxylamine, the title compound was prepared in 36% yield as the sodium salt, m.p. 117–120° C. (dec.).

Spectroscopic data was as follows:

$^1$H NMR (DMSO-d$_6$, 90 MHz): δ=7.908 (1H, s, nitronyl CH), 7.445 (1H, d, J=3.3 Hz, furan CH), 6.486 (1H, d, J=3.3 Hz, furan CH), and 1.430 (9H, s, 3 CH$_3$).

Example 5

Synthesis of N-n-Hexyl-α-(2-sulfofuran-5-yl) nitrone

Following the procedure of Example 1 above and using 5-formylfuran-2-sulfonic acid, sodium salt hydrate and N-n-hexylhydroxylamine, the title compound was prepared in 76% yield as the sodium salt, m.p. 225.5° C. (dec.).

Spectroscopic data was as follows:

IR (KBr, cm$^{-1}$): 2956.8 (CH), 2927.1 (CH), 1617.2 (C=N), 1247.6 (SO$_3$), 1222.7 (SO$_3$) and 1171.2 (N—O).

$^1$H NMR (DMSO-d$_6$, 270 MHz): δ=8.050 (1H, s, nitronyl CH), 7.448 (1H, d, J=2.2 Hz, furan CH), 6.517 (1H, d, J=2.2 Hz, furan CH), 3.890 (2H, t, J=6.6 Hz, CH$_2$), 1.779 (2H, m, CH$_2$), 1.263 (2H, m, CH$_2$CH$_2$CH$_2$) and 0.850 (3H, t, CH$_3$).

$^{13}$C NMR (DMSO-d$_6$, 270 MHz): δ=158.275, 146.866, 125.069, 113.964, 110.258, 64.772, 30.895, 27.142, 25.526, 22.078 and 13.948.

Example 6

Synthesis of N-Cyclohexyl-α-(2sulfofuran-5-yl) nitrone

Following the procedure of Example 1 above and using 5-formylfuran-2-sulfonic acid, sodium salt hydrate and N-cyclohexylhydroxylamine, the title compound was prepared in 84.3% yield as the sodium salt, m.p. 236.1° C. (dec.).

Spectroscopic data was as follows:

IR (KBr, cm$^{-1}$): 2934.2 (CH), 2858.4 (CH), 1637.2 (C=N), 1215.5 (SO$_3$) and 1168.9 (N—O).

$^1$H NMR (DMSO-d$_6$, 270 MHz): δ=8.015 (1H, s, nitronyl CH), 7.439 (1H, d, J=3.5 Hz, furan CH), 6.508 (1H, d, J=3.5 Hz, furan CH), 4.053 (1H, m, NCH) and 1.814–1.097 (10H, m, 5 CH$_2$).

$^{13}$C NMR DMSO-d$_6$, 270 MHz): δ=158.230, 147.049, 123.208, 113.858, 110.197, 72.597, 30.666, 24.839 and 24.534.

Example 7

Synthesis of N-tert-Octyl-α-(2-sulfofuran-5-yl) nitrone

Following the procedure of Example 1 above and using 5-formylfuran-2-sulfonic acid, sodium salt hydrate and N-tert-octylhydroxylamine, the title compound was prepared in 98% yield as the sodium salt, m.p. 216.9° C. (dec.).

Spectroscopic data was as follows:

IR (KBr, cm$^{-1}$): 2954.3 (CH), 2905.4 (CH), 1634.8 (C=N), 1216 (SO$_3$) and 1168.3 (N—O).

$^1$H NMR (DMSO-d$_6$, 270 MHz): δ=8.031 (1H, s, nitronyl CH), 7.492 (1H, d, J=3.5 Hz, furan CH), 6.517 (1H, d, J=3.5 Hz, furan CH), 1.844 (2H, s, CH$_2$), 1.525 (6H, s, 2 CH$_3$) and 0.885 (9H, s, 3 CH$_3$).

$^{13}$C NMR (DMSO-d$_6$, 270 MHz): δ=158.336, 147.857, 122.079, 113.873, 110.182, 72.796, 50.983, 31.398, 30.452 and 28.332.

Example 8

Synthesis of N-Adamantyl-α-(2-sulfofuran-5-yl) nitrone

Following the procedure of Example 1 above and using 5-formylfuran-2-sulfonic acid, sodium salt hydrate and N-adamantylhydroxylamine, the title compound was prepared in 59% yield as the sodium salt, m.p. 236.9° C. (dec.).

Spectroscopic data was as follows:

IR (KBr, cm$^{-1}$): 2910.7 (CH), 2853.0 (CH), 1638 (C=N), 1216.8 (SO$_3$) and 1168.4 (N—O).

$^1$H NMR (DMSO-d$_6$, 270 MHz): δ=7.849 (1H, s, nitronyl CH), 7.495 (1H, d, J=3.5 Hz, furan CH), 6.518 (1H, d, J=3.5 Hz, furan CH), 2.166 (3H, bs, 3 CH), 2.075 (6H, bs, 3 CH$_2$) and 1.666 (6H, bs, 3 CH$_2$).

$^{13}$C NMR (DMSO-d$_6$, 270 MHz): δ=158.306, 147.644, 120.417, 114.087, 110.288, 69.669, 35.639 and 29.293.

Example 9

Synthesis of N-Benzyl-α-(2sulfofuran-5-yl)nitrone

Following the procedure of Example 1 above and using 5-formylfuran-2-sulfonic acid, sodium salt hydrate and N-benzylhydroxylamine, the title compound was prepared in 82% yield as the sodium salt, m.p. 223.7° C. (dec.).

Spectroscopic data was as follows:

IR (KBr, cm$^{-1}$): 3079.2 (aromatic CH), 1632.4 (C=N), 1242.2 (SO$_3$), 1219 (SO$_3$) and 1173.1 (N—O).

$^1$H NMR (DMSO-d$_6$, 270 MHz): δ=8.273 (1H, s, nitronyl CH), 7.500–7.371 (6H, m, C$_6$H$_5$ & furan CH), 6.519 (1H, d, J=3.5 Hz, furan CH) and 5.067 (2H, s, CH$_2$).

$^{13}$C NMR (DMSO-d$_6$, 270 MHz): δ=158.596, 146.790, 135.319, 129.752, 129.126, 125.084, 114.224, 110.304 and 68.738.

Example 10

Synthesis of N-Isopropyl-α-(2,4-disulfofuran-5-yl) nitrone

Following the procedure of Example 1 above and using 5-formylfuran-2,4-disulfonic acid disodium salt and N-isopropylhydroxylamine, the title compound could be prepared as the disodium salt.

Example 11

Synthesis of N-Isopropyl-α-[2-(N-morpholinosulfonyl)furan-5-yl]nitrone

To a mixture of POCl$_3$, (16.0 mL, 171.66 mmol) and 5-formyl-2-furansulfonic acid sodium salt (15.0 g, 75.71 mmol) was added PCl$_5$ (38.0 g, 182.48 mmol) in portions over a 20 min. period with cooling. The mixture was stirred at room temperature for additional 90 min. The solids (primarily NaCl) were removed by filtration and washed with CH$_2$Cl$_2$ (25 mL). Rotary evaporation of the filtrate gave crude 5-dichloromethyl-2-furansulfonyl chloride (16.43 g). This liquid was dissolved in Et$_2$O or CH$_2$Cl$_2$ (100 mL) and cooled to −45° C. A solution of morpholine (12.0 mL, 138.20 mmol) in Et$_2$O or CH$_2$Cl$_2$ (30 mL) was added dropwise during 15 min. After stirring for 1 h at room temperature, the mixture was filtered and the solid was washed with 2×60 mL of the solvent. The combined filtrates were rotary evaporated to provide crude 2-(N-morpholinosulfonyl)-5-dichloromethylfuran (15.13 g) as a yellowish crystalline solid. Part of this solid (14.13 g, 47.07 mmol) was dissolved in 75% HCOOH (75 mL) and refluxed for 60 min. The solution was then rotary evaporated to afford crude 2-(N-morpholinosulfonyl)-5-furaldehyde (12.58 g) as a brown solid. This solid was mixed with molecular sieves (55 g), silica gel (10 g) and Me$_2$CHNHOH (6.0 g, 80 mmol) in CHCl$_3$ (250 mL) under argon. After stirring at room temperature for 1 h, the mixture was filtered and rotary evaporated to produce a yellowish solid. This crude product was recrystallized from hexanes and ethylene glycol dimethyl ether to give the title compound (6.92 g, 30.2% overall yield) as a solid, m.p.=163.7° C. R$_f$=0.31 on a silica gel plate using EtOAc as the eluant).

Spectroscopic data was as follows:

IR (KBr, cm$^{-1}$): 2982 (CH), 2934 (CH), 2872 (CH), 1634 (C=N), 1584 (furan ring), 1364.8 (SO$_2$), 1188.1 (N—O), 1149.3 (SO2), 1112.7 (C—O—C).

$^1$H NMR (CDCl$_3$, 270 MHz): δ=7.763 (1H, d, J=3.6 Hz, furan CH), 7.649 (1H, s, nitronyl CH), 7.091 (1H, d, J=3.6 Hz, furan CH), 4.218 (1H, septet, J=6.6 Hz, CH), 3.718 (4H, m, CH$_2$OCH$_2$), 3.150 (4H, m, CH$_2$NCH$_2$) and 1.472 (6H, d, J=6.6 Hz, 2 CH$_3$).

$^{13}$C NMR (CDCl$_3$, 270 MHz): δ=150.801, 145.920, 122.018, 119.349, 114.605, 67.457, 65.947, 45.614 and 20.538.

Example 12

Synthesis of N-Isopropyl-α-[2-(N,N-dimethylsulfamoyl)furan-5yl]nitrone

The title compound was prepared using the procedure described in Example 11 above and using N,N-dimethylamine instead of morpholine. The title compound was isolated in 32.1% yield as a solid, m.p.=79.0° C. (R$_f$=0.35 on a silica gel plate using EtOAc as the eluant).

Spectroscopic data was as follows:

IR (KBr, cm$^{-1}$): 2980 (CH), 1640 (C=N), 1582 (furan ring), 1356.0 (SO$_2$), 1177.6 (N—O) and 1136.9 (SO$_2$).

$^1$H NMR (CDCl$_3$, 270 MHz): δ=7.747 (1H, d, J=3.7 Hz, furan CH), 7.653 (1H, s, nitronyl CH), 7.056 (1H, d, J=3.7 Hz, furan CH), 4.211 (1H, septet, J=6.6 Hz, CH), 2.794 (6H, s, CH$_3$NCH$_3$) and 1.457 (6H, d, J=6.7 Hz, 2 CH3).

$^{13}$C NMR (CDCl$_3$, 270 MHz): δ=150.435, 146.347, 122.186, 118.647, 114.575, 67.320, 37.469 and 20.507.

Example 13

Synthesis of N-Isopropyl-α-[2-(N,N-diethylsulfamoyl)furan-5yl]nitrone

The title compound was prepared using the procedure described in Example 11 above and using N,N-diethylamine instead of morpholine. The title compound was isolated in 40.4% yield as a solid, m.p.=82.9° C. (R$_f$=0.34 on a silica gel plate using EtOAc as the eluant).

Spectroscopic data was as follows:

IR (KBr, cm$^{-1}$): 2981.2 (CH), 2938 (CH), 1633.2 (C=N), 1556.6 (furan ring), 1359.1 (SO$_2$), 1172.4 (N—O) and 1135.4 (SO$_2$).

$^1$H NMR (CDCl$_3$, 270 MHz): δ=7.706 (1H, d, J=3.6 Hz, furan CH), 7.609 (1H, s, nitronyl CH), 7.002 (1H, d, J=3.6 Hz, furan CH), 4.196 (1H, septet, J=6.6 Hz, CH), 3.269 (4H, q, J=7.2 Hz, CH$_2$NCH$_2$), 1.451 (6H, d, J=6.6 Hz, 2 CH$_3$) and 1.120 (6H, t, J=7.2 Hz, 2 CH$_3$).

$^{13}$C NMR (CDCl$_3$, 270 MHz): δ=149.703, 149.123, 122.201, 117.351, 114.758, 67.213, 42.030, 20.491 and 13.674.

Example 14

Synthesis of N-Isopropyl-α-[2-(N-4-methylpiperazin-1-ylsulfonyl)furan-5yl]nitrone The title compound was prepared using the procedure described in Example 11 above and using 1-methylpiperazine instead of morpholine. The title compound was isolated in 35.6% yield as a solid, m.p.=111.5° C. ($R_f$=0.19 on a silica gel plate using EtOAc:EtOH (4:1, v:v) as the eluant).

Spectroscopic data was as follows:

IR (KBr, cm$^{-1}$): 2982 (CH), 2858 (CH), 1634 (C=N), 1582 (furan ring), 1364.6 (SO$_2$), 1182.8 (N—O) and 1142.6 (SO$_2$).

$^1$H NMR (CDCl$_3$, 270 MHz): δ=7.739 (1H, d, J 3.6 Hz, furan CH), 7.618 (1H, s, nitronyl CH), 7.071 (1H, d, J=3.6 Hz, furan CH), 4.204 (1H, septet, J=6.6 Hz, CH), 3.201 (4H, m, CH$_2$NCH$_2$), 2.450 (4H, m, CH$_2$NCH$_2$), 2.263 (3H, s, CH$_3$) and 1.470 (6H, d, J=6.6 Hz, 2 CH$_3$).

$^{13}$C NMR (CDCl$_3$, 270 MHz): δ=150.557, 146.393, 121.957, 118.968, 114.559, 67.381, 53.821, 45.614, 45.523 and 20.538.

Example 15

Synthesis of N-Isopropyl-α-[2-(N-4-methylpiperazin-1-ylsulfonyl)-furan-5-yl]nitrone Hydrochloride Hydrochloride gas was bubbled into a solution of the product from Example 14 above in CH$_2$Cl$_2$. The title compound was isolated in 84.5% as a solid, m.p.=212.6° C. (dec.) ($R_f$=0 on a silica gel plate using EtOAc:EtOH (4:1, v:v) as the eluant).

Spectroscopic data was as follows:

IR (KBr, cm$^{-1}$): 3441.2 (NH), 2984 (CH), 2938 (CH), 2680 (NH$^+$Cl$^-$), 2594 (NH$^+$Cl$^-$), 2452 (NH$^+$Cl$^-$), 1636 (C=N), 1558 (furan ring), 1365.3 (SO$_2$), 1188.7 (N—O) and 1141.2 (SO$_2$).

$^1$H NMR (D$_2$O, 270 MHz): δ=8.205 (1H, s, nitronyl CH), 7.741 (1H, d, J=4.0 Hz, furan CH), 7.443 (1H, d, J=4.0 Hz, furan CH), 4.431 (1H, septet, J=6.5 Hz, CH), 4.018 (2H, broad s, CH$_2$N), 3.613 (2H, broad s, CH$_2$N), 3.270 (4H, broad s, CH$_2$NCH$_2$), 2.942 (3H, s, CH$_3$) and 1.445 (6H, d, J=6.5 Hz, 2 CH$_3$).

$^{13}$C NMR D$_2$O, 270 MHz): δ=150.100, 145.874, 127.967, 120.615, 117.595, 67.243, 52.585, 42.884, 42.762 and 19.440.

Example 16

Synthesis of N-tert-Butyl-α-[2-(N-3-trifluoromethylphenylsulfamoyl)-furan-5-yl]nitrone The title compound was prepared using the procedure described in Example 11 above and using 3-thifluoromethylaniline instead of morpholine and N-tert-butylhydroxylamine instead of N-isopropylhydroxylamine. The title compound was isolated in 14.9% yield as a solid, m.p.=162.1° C. ($R_f$=0.08 on a silica gel plate using CH$_2$Cl$_2$ as the eluant).

Spectroscopic data was as follows:

IR (KBr, cm$^{-1}$): 3094 (aromatic CH), 2982.9 (alkyl CH), 1618.8 (C=N), 1363.0 (CF$_3$), 1332.5 (SO$_2$), 1178.8 (SO$_2$), 1144.1 (C—F) and 1127.6 (N—O).

$^1$H NMR (CDCl$_3$, 270 MHz): δ=7.657–7.627 (3H, m, furan CH, nitronyl H & phenyl H), 7.433 (1H, s, NHSO$_2$), 7.401–7.329 (3H, m, phenyl H's), 7.085 (1H, d, J=3.5 Hz, furan CH) and 1.549 (9H, s, 3 CH$_3$).

$^{13}$C NMR (CDCl$_3$, 270 MHz): δ=151.442, 146.622, 136.661, 132.154 (q, J=32.8 Hz), 130.347, 124.260, 123.666 (q, J=274.1 Hz), 122.415, 120.508, 119.852, 117.885, 114.392, 71.301 and 27.661.

Example 17

Synthesis of N-tert-Butyl-α-[2-(methylsulfonyl)-furan-5yl]nitrone

A solution of 5-bromo-2-furaldehyde (20 g, 0.1143 mol) and methanesulfinic acid sodium salt (25 g, 0.2427 mol) in 2-ethoxyethanol (300 mL) was refluxed for 3 h and poured into ice-water (1000 g) after cooling. The mixture was extracted with CHCl$_3$ and the CHCl$_3$ solution was dried over Na$_2$SO$_4$, filtered and rotary evaporated. The resulting residue (9.16 g) was reacted with N-tert-butylhydroxylamine (7.0 g) in CHCl$_3$ in the presence of molecular sieves (4A, 50 g) and silica gel (10 g) at room temperature for 21 h and at refluxing temperature for 3 h. After filtration and evaporation, the residue obtained was purified by column chromatography eluted with hexanes and ethyl acetate (1:1, v:v) to give the title compound (5.37 g, 19.2% overall yield) as a solid, m.p. 137.5° C. ($R_f$=0.27 on a silica gel plate using hexanes/EtOAc (1:1, v:v) as the eluant).

Spectroscopic data was as follows:

IR (KBr, cm$^{-1}$): 3173.2 (furan CH), 2997.0 (alkyl CH), 2915.1 (alkyl CH), 1636 (C=N), 1320.9 (SO$_2$), 1173.0 (SO$_2$) and 1127.6 (N—O).

$^1$H NMR (CDCl$_3$, 270 MHz): δ=7.792 (1H, s, nitronyl CH), 7.757 (1H, d, J=3.6 Hz, furan CH), 7.204 (1H, d, J=3.6 Hz, furan CH), 3.126 (3H, s, CH$_3$) and 1.549 (9H, s, 3 CH$_3$).

$^{13}$C NMR (CDCl$_3$, 270 MHz): δ=151.930, 148.818, 120.386, 119.181, 114.407, 71.270, 43.235 and 27.737.

Using the procedures described in Examples 1–17 above and the appropriate starting materials and reagents, the following furan nitrone compounds of formula I could be prepared:

N-methyl-α-(2-sulfofuran-3-yl)nitrone
N-methyl-α-(2-sulfofuran-4-yl)nitrone
N-methyl-α-(2-sulfofuran-5-yl)nitrone
N-methyl-α-(3-sulfofuran-2-yl)nitrone
N-methyl-α-(3-sulfofuran-4-yl)nitrone
N-methyl-α-(3-sulfofuran-5-yl)nitrone
N-ethyl-α-(2-sulfofuran-3-yl)nitrone
N-ethyl-α-(2-sulfofuran-4-yl)nitrone
N-ethyl-α-(2-sulfofuran-5-yl)nitrone
N-ethyl-α-(3-sulfofuran-2-yl)nitrone
N-ethyl-α-(3-sulfofuran-4-yl)nitrone
N-ethyl-α-(3-sulfofuran-5-yl)nitrone
N-n-propyl-α-(2-sulfofuran-3-yl)nitrone
N-n-propyl-α-(2-sulfofuran-4-yl) nitrone
N-n-propyl-α-(3-sulfofuran-2-yl)nitrone
N-n-propyl-α-(3-sulfofuran-4-yl)nitrone
N-n-propyl-α-(3-sulfofuran-5-yl)nitrone
N-isopropyl-α-(2-sulfofuran-3-yl)nitrone
N-isopropyl-α-(2-sulfofuran-4-yl)nitrone
N-isopropyl-α-(3-sulfofuran-2-yl)nitrone
N-isopropyl-α-(3-sulfofuran-4-yl)nitrone
N-isopropyl-α-(3-sulfofuran-5-yl)nitrone N-n-butyl-α-(2-sulfofuran-3-yl)nitrone
N-n-butyl-α-(2-sulfofuran-4-yl)nitrone
N-n-butyl-α-(3-sulfofuran-2-yl)nitrone
N-n-butyl-α-(3-sulfofuran-4-yl)nitrone
N-n-butyl-α-(3-sulfofuran-5-yl)nitrone
N-sec-butyl-α-(2-sulfofuran-3-yl)nitrone
N-sec-butyl-α-(2-sulfofuran-4-yl)nitrone
N-sec-butyl-α-(2-sulfofuran-5-yl)nitrone
N-sec-butyl-α-(3-sulfofuran-2-yl)nitrone
N-sec-butyl-α-(3-sulfofuran-4-yl)nitrone
N-sec-butyl-α-(3-sulfofuran-5-yl)nitrone
N-isobutyl-α-(2-sulfofuran-3-yl)nitrone
N-isobutyl-α-(2-sulfofuran-4-yl)nitrone
N-isobutyl-α-(2-sulfofuran-5-yl)nitrone
N-isobutyl-α-(3-sulfofuran-2-yl)nitrone
N-isobutyl-α-(3-sulfofuran-4-yl)nitrone
N-isobutyl-α-(3-sulfofuran-5-yl)nitrone
N-tert-butyl-α-(2-sulfofuran-3-yl)nitrone
N-tert-butyl-α-(2-sulfofuran-4-yl)nitrone
N-tert-butyl-α-(3-sulfofuran-2-yl)nitrone
N-tert-butyl-α-(3-sulfofuran-4-yl)nitrone
N-tert-butyl-α-(3-sulfofuran-5-yl)nitrone
N-n-hexyl-α-(2-sulfofuran-3-yl)nitrone
N-n-hexyl-α-(2-sulfofuran-4-yl)nitrone
N-n-hexyl-α-(3-sulfofuran-2-yl)nitrone
N-n-hexyl-α-(3-sulfofuran-4-yl)nitrone
N-n-hexyl-α-(3-sulfofuran-5-yl)nitrone
N-cyclohexyl-α-(2-sulfofuran-3-yl)nitrone
N-cyclohexyl-α-(2-sulfofuran-4-yl)nitrone
N-cyclohexyl-α-(3-sulfofuran-2-yl)nitrone
N-cyclohexyl-α-(3-sulfofuran-4-yl)nitrone
N-cyclohexyl-α-(3-sulfofuran-5-yl)nitrone
N-tert-octyl-α-(2-sulfofuran-3-yl)nitrone
N-tert-octyl-α-(2-sulfofuran-4-yl)nitrone
N-tert-octyl-α-(3-sulfofuran-2-yl)nitrone
N-tert-octyl-α-(3-sulfofuran-4-yl)nitrone
N-tert-octyl-α-(3-sulfofuran-5-yl)nitrone
N-benzyl-α-(2-sulfofuran-3-yl)nitrone
N-benzyl-α-(2-sulfofuran-4-yl)nitrone
N-benzyl-α-(3-sulfofuran-2-yl)nitrone
N-benzyl-α-(3-sulfofuran-4-yl)nitrone
N-benzyl-α-(3-sulfofuran-5-yl)nitrone
N-methyl-α-[2-(N-methylsulfamoyl)furan-5-yl]nitrone
N-ethyl-α-[2-(N-methylsulfamoyl)furan-5-yl]nitrone
N-n-propyl-α-[2-(N-methylsulfamoyl)furan-5-yl]nitrone
N-isopropyl-α-[2-(N-methylsulfamoyl)furan-5-yl] nitrone
N-n-butyl-α-[2-(N-methylsulfamoyl)furan-5-yl]nitrone
N-isobutyl-α-[2-(N-methylsulfamoyl)furan-5-yl]nitrone
N-sec-butyl-[2-(N-methylsulfamoyl)furan-5-yl]nitrone
N-tert-butyl-α-[2-(N-methylsulfamoyl)furan-5-yl]nitrone
N-n-hexyl-α-[2-(N-methylsulfamoyl)furan-5-yl]nitrone
N-cyclohexyl-α-[2-(N-methylsulfamoyl)furan-5-yl] nitrone
N-tert-octyl-α-[2-(N-methylsulfamoyl)furan-5-yl]nitrone
N-benzyl-α-[2-(N-methylsulfamoyl)furan-5-yl]nitrone
N-methyl-α-(2,4-disulfofuran-5-yl)nitrone
N-ethyl-α-(2,4-disulfofuran-5-yl)nitrone
N-n-propyl-α-(2,4-disulfofuran-5-yl)nitrone
N-isopropyl-α-(2,4-disulfofuran-5-yl)nitrone
N-n-butyl-α-(2,4disulfofuran-5-yl)nitrone
N-isobutyl-α-(2,4-disulfofuran-5-yl)nitrone
N-sec-butyl-α-(2,4-disulfofuran-5-yl)nitrone
N-tert-butyl-α-(2,4-disulfofuran-5-yl)nitrone
N-n-hexyl-α-(2,4-disulfofuran-5-yl)nitrone
N-cyclohexyl-α-(2,4-disulfofuran-5-yl)nitrone
N-tert-octyl-α-(2,4-disulfofuran-5-yl)nitrone
N-benzyl-α-(2,4-disulfofuran-5-yl)nitrone
N-methyl-α-(2,3-disulfofuran-5-yl)nitrone
N-ethyl-α-(2,3-disulfofuran-5-yl)nitrone
N-n-propyl-α-(2,3-disulfofuran-5-yl)nitrone
N-isopropyl-α-(2,3-disulfofuran-5-yl)nitrone
N-n-butyl-α-(2,3-disulfofuran-5-yl)nitrone
N-isobutyl-α-(2,3-disulfofuran-5-yl)nitrone
N-sec-butyl-α-(2,3-disulfofuran-5-yl)nitrone
N-tert-butyl-α-(2,3-disulfofuran-5-yl)nitrone
N-n-hexyl-α-(2,3-disulfofuran-5-yl)nitrone
N-cyclohexyl-α-(2,3-disulfofuran-5-yl)nitrone
N-tert-octyl-α-(2,3-disulfofuran-5-yl)nitrone
N-benzyl-α-(2,3-disulfofuran-5-yl)nitrone
N-methyl-α-[2,4-di(N-methylsulfamoyl)furan-5-yl] nitrone
N-ethyl-α-[2,4-di(N-methylsulfamoyl)furan-5-yl]nitrone
N-n-propyl-α-[2,4-di(N-methylsulfamoyl)furan-5-yl] nitrone
N-isopropyl-α-[2,4-di(N-methylsulfamoyl)furan-5-yl] nitrone
N-n-butyl-α-[2,4-di(N-methylsulfamoyl)furan-5-yl] nitrone
N-isobutyl-α-[2,4-di(N-methylsulfamoyl)furan-5-yl] nitrone
N-sec-butyl-α-[2,4-di(N-methylsulfamoyl)furan-5-yl] nitrone
N-tert-butyl-α-[2,4-di(N-methylsulfamoyl)furan-5-yl] nitrone
N-n-hexyl-α-[2,4-di(N-methylsulfamoyl)furan-5-yl] nitrone
N-cyclohexyl-α-[2,4-di(N-methylsulfamoyl)furan-5-yl] nitrone
N-tert-octyl-α-[2,4-di(N-methylsulfamoyl)furan-5-yl] nitrone
N-benzyl-α-[2,4-di(N-methylsulfamoyl)furan-5-yl] nitrone and the like; and pharmaceutically acceptable salts thereof, including but not limited to, the sodium, potassium, and calcium monocitrate salts.

Example 18

Free Radical Trapping

In this example, the ability of furan nitrones of formula I above to trap free radicals in vitro is demonstrated. Free radicals have been implicated in Alzheimer's disease and other long term neurodegenerative conditions. A series of studies were conducted to determine the ability of furan nitrones to trap free radicals in biological settings.

Dichlorofluorescein (DCF) is a compound that fluoresces when oxidized by reactive oxygen species (ROS), such as hydroxyl, peroxyl, or alkoxyl free radicals. Test compounds were evaluated for their ability to scavenge radicals by determining their capacity to prevent the DCF oxidation in a radical generating environment. Two radical generating systems were used: (i) ferrous iron and (ii) tert-butyl hydroperoxide. When ferrous iron is placed in normoxic solution, it auto-oxidizes to produce ROS in the form of hydroxyl radicals, superoxide anion free radicals, and hydrogen peroxide. Similarly, when tert-butyl hydroperoxide is placed in non-chelated media, trace metals catalyze its oxidation to yield alkoxy, peroxyl, and alkyl free radicals.

In this assay, either 100 μM $FeSO_4$ or 25 μM tert-butyl hydroperoxide were mixed with 50 μM DCF and 100 μM of the test compound in MEM and the mixture was incubated at 37° C. for 2 hrs. The fluorescence wavelengths measured were 485 nm for excitation and 530 nm for emission. In these tests, N-isopropyl-α-(2-sulfofuran-5-yl)nitrone sodium salt (prepared in Example 1 above) reduced fluorescence by 20% in the $Fe^{+2}$ assay and by 13% in the tert-butyl hydroperoxide assay. In comparison, a known free radical trap, N-tert-butyl-α-phenylnitrone (PBN) reduced fluorescence by 48% in the $Fe^{+2}$ assay and by 9% in the tert-butyl hydroperoxide assay. These results demonstrate that N-isopropyl-α-(2-sulfofuran-5-yl)nitrone sodium salt was effective at trapping free radicals.

Example 19

Electron Spin Resonance (ESR) Study

In this experiment, the ability of furan nitrones of formula I above to trap free radicals is demonstrated using ESR spin trapping techniques. See, for example, K. R. Maples et al., "In Vivo Detection of Free Radical Metabolites", *Free Radicals in Synthesis and Biology* (F. Minisci, ed.) pp. 423–436 (Kluwer Academic Publishers, Boston, 1989); and J. A. DeGray et al., "Biological Spin Trapping", *Electron Spin Resonance* 14:246–300 (1994). A t-butyl hydroperoxide/ferrous iron free radical generating system was used in this experiment. This free radical generating system produces t-butyl-alkoxyl radicals, t-butyl-peroxyl radicals, and methyl radicals. If the furan nitrones are capable of trapping any of these radicals, radical adducts should be detectable by ESR spectroscopy.

To 490 μl of a 100 mM solution of N-isopropyl-α-(2-sulfofuran-5-yl)nitrone sodium salt in water was added 5 μl of 1 mM t-butyl hydroperoxide. The reaction was initiated by the addition of 5 μl of 1 mM ferrous sulfate and then the solution was quickly transferred into a quartz flat cell and this cell was placed in the cavity of a Bruker ESP 300 ESR spectrometer. ESR spectrometer settings were: 9.75 GHz frequency, 10 dB power, $8\times10^4$ receiver gain, 0.20 G modulation amplitude, 0.080 sec time constant, 3480 G center field, 200 G sweep width and 240 sec sweep time.

As shown in FIG. 1, N-isopropyl-α-(2-sulfofuran-5-yl) nitrone sodium salt reacted with radicals generated by the t-butyl hydroperoxide/ferrous iron system to produce a radical adduct. The adduct is characterized as a 4.5 G doublet of 4.5 G doublet of 16.5 G 1:1:1 triplets. The hyperfine splittings arise from couplings of the electron with the magnetic moment of the hydrogen atoms attached to the N-isopropyl group, the hydrogen atom attached to the nitrone carbon and from the nitrogen of the nitrone. Based on the large $a_H$ splitting, and in comparison to similar results previously reported for N-tert-butyl-α-phenylnitrone, the species trapped is most likely a methyl radical. Thus, the ESR spectrum shown in FIG. 1 demonstrates that N-isopropyl-α-(2-sulfofuran-5-yl)nitrone sodium salt was effective at trapping free radicals and can be used as an analytical reagent for ESR applications.

Example 20

Treatment of Acute CNS Disorders

Figure 2:
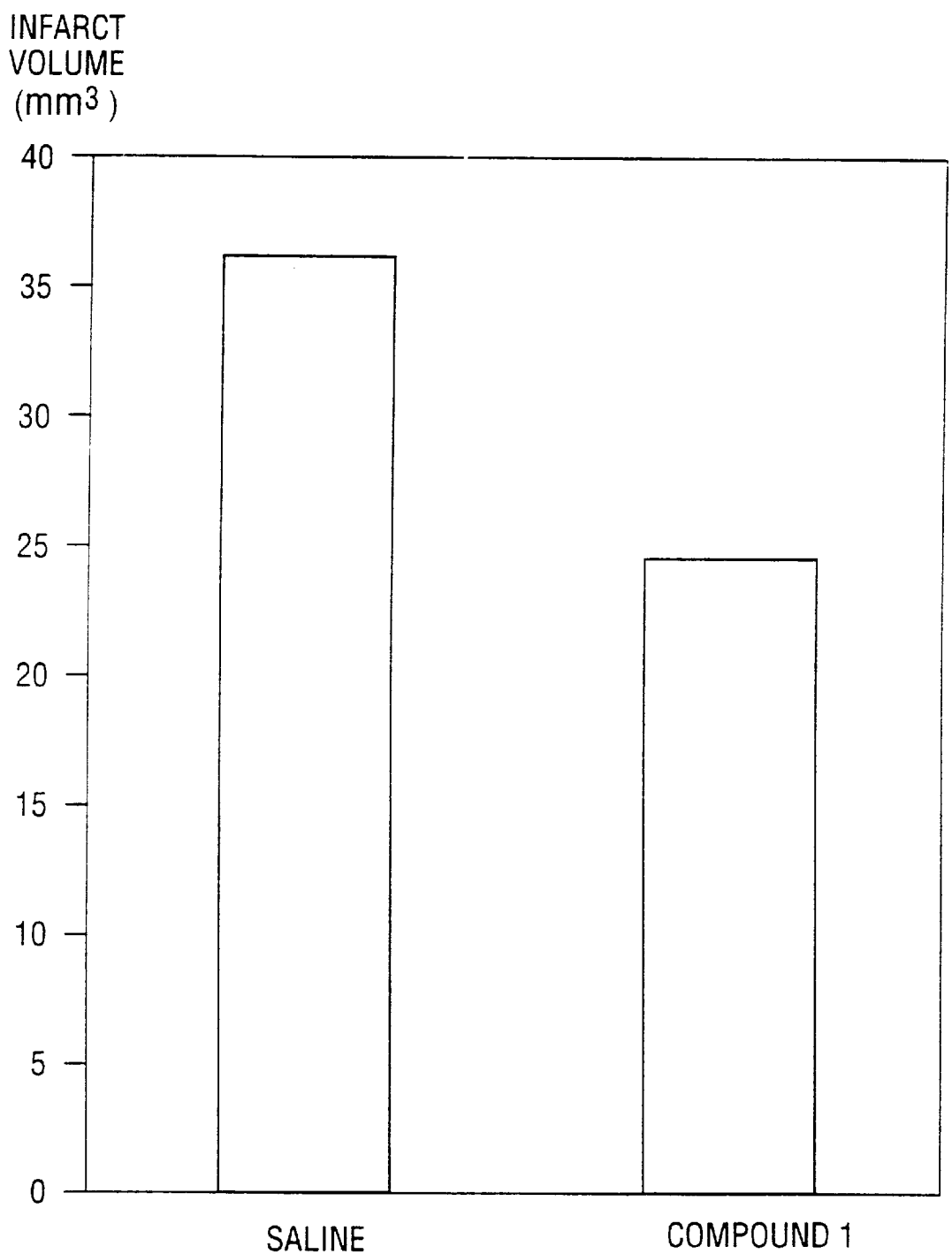
FIG. 2 is a bar graph illustrating the infarct volume for surgically-induced strokes in rodents treated with a furan nitrone of formula I (Compound 1) or a saline control.

In this example, the ability of a furan nitrone of formula I above to reduce the infarct volume in an in vivo stroke model is demonstrated. A rat permanent middle cerebral artery occlusion (MCAO) model was used to determine stroke treatment efficacy. MCAO is a representative model of acute CNS disorders. See, for example, M. D. Ginsberg et al., "Rodent Models of Cerebral Ischemia" (1989) Stroke, 20:1627–1642. In this stroke model, the middle cerebral artery was permanently occluded via cauterization to produce a focal stroke. N-isopropyl-α-(2-sulfofuran-5-yl) nitrone, sodium salt (prepared in Example 1 above) was then administered as a 10 mg/kg i.v. bolus dose three hours post MCAO through a catheter surgically implanted in the jugular vein. Two days post MCAO, the rats were sacrificed and the extent of brain damage assessed using tetrazolium staining (TTC staining) followed by computer image analysis to quantitate infarct volumes, i.e., the regions of dead tissue. The mean infarct volume for rats treated with the test compound was 24.7 $mm^3$ whereas the mean infarct volume for rats not treated with the test compound was 36.0 $mm^3$. These results are illustrated in FIG. 2. Thus, N-isopropyl-α-(2-sulfofuran-5-yl)nitrone, sodium salt reduced the mean infarct volume of a stroke by 32% when administered three hours post stroke compared to controls.

Example 21

Inhibition of Aβ Beta-Pleated Sheet Formation

The deposition of amyloid β-peptide (Aβ) is associated with the development of Alzheimer's disease. See, for example, G. G. Glenner et al. (1984) *Biochem. Biophys. Res. Commun.*, 120:885–890; and R. E. Tanzi (1989) *Ann. Med.*, 21:91–94. Accordingly, compounds which effectively disrupt the formation of Aβ(1–40) or Aβ(1–42) beta-pleated sheets are potentially useful for preventing and/or reversing such amyloid deposits. Thioflavin T (ThT) is known to rapidly associate with beta-pleated sheets, particularly the aggregated fibrils of synthetic Aβ(1–40). This association gives rise to a new excitation maximum at 440 nm and to enhanced emission at 490 nm. In this experiment, the ability of furan nitrones of formula I above to inhibit the association of ThT with synthetic Aβ(1–40) or Aβ(1–42) is demonstrated by measuring changes in fluorescence.

The experiments were performed using a CytoFluor II fluorescence plate reader having the following parameters:

Filters: Excitation 440 nm/20 Emission 490 nm/40

Gam: 75

Cycle to Cycle Time: 30 min

Run Time: 720 min (24 cycles) or dependent on experimental design

Plate: 96 well

Into each well was aliquoted 95 μl of ThT (3 μM) prepared in PBS (pH 6.0), 2 μL of the compound to be tested (10 μM) prepared with 0.05% of methylcellulose in PBS (pH 6.0), and 3 μL of Aβ(1–40)(3 μg) prepared with $dH_2O$ (the compounds prepared in Examples 1, 3, 4, 5, 6, 7, 8, 9, 11 and 12 were tested). The fluorescence measurement began when the Aβ(1–40) was added and continued for a total of 12 hours. The percent inhibition of beta-pleated sheet formation was calculated from the relative fluorescence unit difference between aggregation in the presence and in the absence of the test compounds. The data show that the compounds prepared in Examples 1, 5, 6, 7, 9, 11 and 12 above inhibited Aβ(1–40) beta-pleated sheet formation 15 to 71% compared to the controls. At 10 μM, the compounds prepared in Examples 3, 4, and 8 above did not significantly reduce Aβ(1–40) beta-pleated sheet formation in this test.

In experiments conducted in a similar manner using Aβ(1–42) instead of Aβ(1–40), the compound prepared in Examples 1, 13, 14 and 15 above inhibited Aβ(1–42) beta-pleated sheet formation by 32 to 55% compared to the controls.

Example 22

Protection Against Aβ(25–35)-Induced Neuronal Cell Loss

Patients with Alzheimer's disease are known to suffer a progressive loss of neuronal cells. See, for example, P. J. Whitehause et al., (1982) Science, 215:1237–1239. In this experiment, the ability of certain furan nitrones of formula I above to protect against Aβ(25–35)-induced neuronal cell loss is demonstrated. Sprague Dawley rat hippocampus of 18-day-gestation embryos was excised and then dissociated by trituration to prepare primary neuronal/astrocyte cultures. Cells ($3\times10^5$) were plated on 35 mm poly-D-lysine-coated plates containing Eagle's minimum essential medium supplemented with 10% fetal bovine serum. After 3–5 hours, the original medium was removed and replaced with 1 mL of fresh medium. Cultures were maintained at 37° C. in a 5% $CO_2$/95% air humidified incubator.

To the cells (7 DIV) was added 30 μM of Aβ(25–35) dissolved in $dH_2O$ (stored at −20° C.) and 100 μM of the test compound (i.e., a compound of Example 1, 3, 4, 5, 6, 7, 8, 12 or 13 above) in 1% methylcellulose. Controls were also conducted without the test compound. The percentage of morphologically viable neurons was determined counting the number of viable neurons after 96 hours treatment compared to the number of neurons before treatment in the same premarked culture regions (three regions/culture, n=6). The data show that the compounds prepared in Example 1, 3, 5, 6, 7, 8 and 13 above reduced Aβ(25–35)-induced neuronal cell loss by 3 to 62% compared to the controls. At 100 μM, the compounds prepared in Examples 4 and 13 above did not significantly reduce Aβ(25–35)-induced neuronal cell loss in this test.

In experiments conducted in a similar manner using Aβ(1–40) instead of Aβ(25–35), the compound prepared in Example 1 above reduced Aβ(1–40)-induced neuronal cell loss by 46% compared to the controls.

Example 23

Reduction of Inflammation

In Alzheimer's disease, stroke and multiple sclerosis, researchers have implicated an inflammatory response in the etiology of the disease. See, for example, P. S. Aisen et al., (1994) Am. J. Psychiatry, 151:1105–1113; D. W. Dickson et al., (1993) Glia, 7:75–83; and S. D. Yan et al., Proc. Natl. Acad. Sci. USA, 94, 5296 (1997). This response has been modeled in cell culture by utilizing various factors to simulate the inflammatory response. Such factors include lipopolysaccharide (LPS), an agent known to cause the expression of nitric oxide and other cytokines; and interferon γ (INF-γ), another agent implicated in the inflammatory/cytokine response. In this example, the ability of furan nitrones of formula I above to reduce the inflammation caused by LPS and INF-γ is demonstrated.

In this experiment, the cell culture system used was composed of E16 rat pure cortical neuronal cells (treated with 10 μM Ara C to retard astrocyte growth) that had been plated on a confluent bed of two week old cortical glial cells prepared from the cortices of 1 day old rat pups and allowed to grow for one week. To these cells was added LPS (20 μg/mL), IL-1β (40 mg/pg/mL), and INF-γ (200 U/mL), either with or without 100 μM of the test compound (i.e., a compound of Example 1, 6, 11, 12, 13, 14 or 15 above). Two days later, cell viability was assessed using the lactate dehydrogenase (LDH) assay to monitor cytosolic protein leakage due to cell membrane damage. The results show that the compounds of Examples 1, 6, 11, 12, 13, 14 and 15 above reduced the inflammation caused by LPS and INF-γ by from 5 to 43% compared to the control.

Example 24

Reduction of β-Amyloid-Induced Increased Cytokine Release

In this experiment, the ability of furan nitrones of formula I to reduce the β-amyloid-induced increased release of cytokines, such as interleukin-1β (IL-1β) is demonstrated. THP-1 cells, a human monocyte cell line from American Type Culture Collection, were grown in RPMI-1640 medium plus 10% fetal bovine serum (FBS, not heat-inactivated) in T-flasks. The medium was changed every two days by spinning down (800 rpm, 5 minutes) the cells and added the same fresh medium. Alternatively, the cultures were maintained by the addition of fresh medium. The cultures were maintained at a cell concentration ranging from between $1\times10^5$ and $1\times10^6$ cells/mL. Because sera may contain unknown factors which can affect macrophage/monocyte IL-1 production, the FBS was reduced to 5% for 24 hours. The FBS was further reduced to 2% over two days prior to starting each experiment. The cells were collected by centrifugation and resuspended to 2% FBS. Cell numbers were calculated and cells were plated on 24-well plates ($3\times10^5$ cells/0.6 mL/well). Cells were then treated with LPS (0.5 μg/ml or 0–10 μg/ml for LPS dose-response experiments) alone or in combination with Aβ peptides (5 μM or 0.05–5 μM for dose-response experiments). When determining the effect of the test compounds on cytokine release, 100 μM of the test compound was added with the LPS and Aβ25–35 and this mixture was incubated for 48 hours prior to performing ELISA.

IL-1β secretions into medium by LPS-stimulated THP-1 cells, in the presence or absence of amyloid peptides and a test compound, were assayed with a commercially available ELISA kit (R & D Systems). Briefly, a microtiter plate coated with a murine monoclonal antibody to human IL-1β was supplied by the manufacturer. Standards and samples were pipetted into the wells and any IL-1β present was bound by the immobilized antibody. Unbound proteins were washed away and a horseradish peroxidase-linked polyclonal antibody specific for IL-1β was added to the wells to "sandwich" the IL-1β bound in the initial step. After washing to remove any unbound antibody-enzyme reagent, a substrate solution (1:1 hydrogen peroxide-tetramethylbenzidine, v/v) was added to the wells and color developed in proportion to the amount of IL-1β bound in the initial step. Color development was stopped with 2 N sulfuric acid and the optical density of the standard and the test samples was measured at 450 nm. The amounts of IL-1β present in the samples were calculated based upon a standard curve. Assays were run in quadruplicate wells. The data show that the compounds prepared in Examples 1, 6, 12 and 13 above reduced the β-amyloid-induced increased release of interleukin-1β by 22 to 48% compared to the controls. At 100 μM, the compound prepared in Examples 11, 14 and 15 above did not significantly reduce the β-amyloid-induced increased release of interleukin-1β in this test.

Example 25

Reduction of Locomotor Impairment Due to Aβ-Peptide

In this experiment, the ability of a furan nitrone of formula I above to reduce the in vivo impairment of animals treated with Aβ-peptide is demonstrated. Male Sprague-Dawley rats (250–400 g) were given an ipsilateral injection of 20 μg of Aβ(25–35) into their substantia nigra. Prior to the injection, the rats were fasted overnight and then each received an oral treatment of N-isopropyl-α-(2-sulfofuran-5-yl)nitrone sodium salt (prepared in Example 1 above) (1–100 mg/kg) dissolved in aqueous 1% methyl cellulose or the vehicle alone, one hour before and three hours post the Aβ-peptide stereotaxic injection. One week after treatment, the rats were dosed s.c. with 0.5 mg/kg apomorphine (dissolved in 0.1% vitamin C in isotonic saline) and the circling reflex was monitored using a Rotorat computerized behavioral monitoring apparatus for the time period between 15 and 30 minutes of being placed in the arena. Impairment of the animals due to Aβ-peptide was determined by measuring the number of rotations over the 15 minute period. A higher number of rotations per period indicates more physical impairment. The data are shown in Table I below.

TABLE I

Locomotor Impairment Due to Aβ(25-35)

| Test No. | Treatment | Rotations Over 15 Minute Period |
|---|---|---|
| 16A | Naive | 4 |
| 16B | Saline | 7 |
| 16C | Aβ(25-35) | 16 |
| 16D | Aβ(25-35) + 100 mg/kg of N-isopropyl-α-(2-sulfofuran-5-yl)nitrone sodium salt | 6 |
| 16E | Aβ(25-35) + 10 mg/kg of N-isopropyl-α-(2-sulfofuran-5-yl)nitrone sodium salt | 9 |

The data in Table I show that N-isopropyl-α-(2-sulfofuran-5-yl)nitrone sodium salt reduced the number of rotations per period and hence, the locomotor impairment, of rats injected with Aβ(25–35) compared to Aβ(25–35)-treated controls.

Example 26

Reduction of Spatial Learning Deficit

In this experiment, the ability of a furan nitrone of formula I above to reduce spatial learning deficiencies in vivo is demonstrated. Treatment of rats with N-nitro-L-arginine, a nitric oxide synthase inhibitor, is known to cause a deficit in spatial learning. See, for example, G. A. Bohme et al., (1993) PNAS, 90:9191–9194. Rats treated with N-nitro-L-arginine wander aimlessly throughout their enclosure whereas untreated rats spend most of their time in the quadrant in which they are initially placed and stay away from the open area in the middle of the enclosure. This N-nitro-L-arginine-induced spatial learning deficit is used as a model for learning deficits caused by Alzheimer's disease and other dementias.

In this experiment, 10 mg/kg of N-isopropyl-α-(2-sulfofuran-5-yl)nitrone sodium salt (prepared in Example 1 above) or a control was administered 30 min before each of nine doses of N-nitro-L-arginine (100 mg/kg. iip.). The wanderings of the rats were then monitored. The results show that rats dosed with N-nitro-L-arginine wander equally around the perimeter of the enclosure and readily cross the center of the field. These results are illustrated in FIG. 2B. In contrast, rats treated with N-nitro-L-arginine and N-isopropyl-α-(2-sulfofuran-5-yl)nitrone sodium salt show a preference for the area of the enclosure into which they were first placed and rarely cross the center of the enclosure as illustrated in FIG. 3C. This behavior is essentially the same as rats treated with a saline control (i.e., without N-nitro-L-arginine) (see FIG. 3A). These results demonstrate that N-isopropyl-α-(2-sulfofuran-5-yl)nitrone sodium salt prevents the spatial learning deficit caused by N-nitro-L-arginine.

Example 27

Prevention of MBP-Induced Experimental Allergic Encephalomyelitis

Multiple sclerosis (MS) is a chronic inflammatory CNS disorder caused by demyelination in the brain and spinal cord. The disease is characterized by progressive CNS dysfunction, including muscular weakness, tremor, incontinence, ocular disturbances, and mental dysfunction, with remissions and exacerbations. At present, the only treatment for MS is physical therapy.

Experimental allergic encephalomyelitis (EAE) induced by injection of myelin basic protein (MBP) or MBP peptide fragments is reported to be a useful model for MS. See, for example, D. E. McFarlin et al., "Recurrent Experimental Allergic Encephalomyelitis in the Lewis Rat," The Journal of Immunology, 113(2): 712–715 (1974). In this experiment, the ability of a furan nitrone of formula I above to prevent MBP-induced EAE is demonstrated.

Acclimated female Lewis rats, (Harlan; 200–250 g) were used in this experiment since this strain of rat is genetically highly susceptible to EAE. In the experiment, 100 mg/kg of N-isopropyl-α-(2-sulfofuran-5-yl)nitrone sodium salt (prepared in Example 1 above) or a vehicle alone (control) was administered po once a day from days 4 to 18. On day 1, the rats received an injection of 100 μg of MBP peptide, from guinea pig brain, plus 500 μg of H37RA Mycobacterium in 0.10 ml complete Freund's adjuvant divided equally between the two hind foot-pads.

The rats were evaluated on a 0–6 scale every day after day 7 until day 18 (effects usually begin day 10 and peak day 15). See E. Heber-Katz, "The Ups and Downs of EAE," International Reviews Immunology, 2: 277–285 (1992). The 0–6 evaluation scale is as follows: 0) normal; 1) abnormal gait, hopping, flaccid tail; 2) definite weakness in one or both hind legs, mild ataxia; 3) moderate paraparesis, severe ataxia; 4) minimal hind leg movement after painful stimuli only; 5) no hind leg movement; 6) moribund state with little or no movement, impaired respiration. Results are expressed as a behavioral score ranging from 0 to 6.

Figure 4:
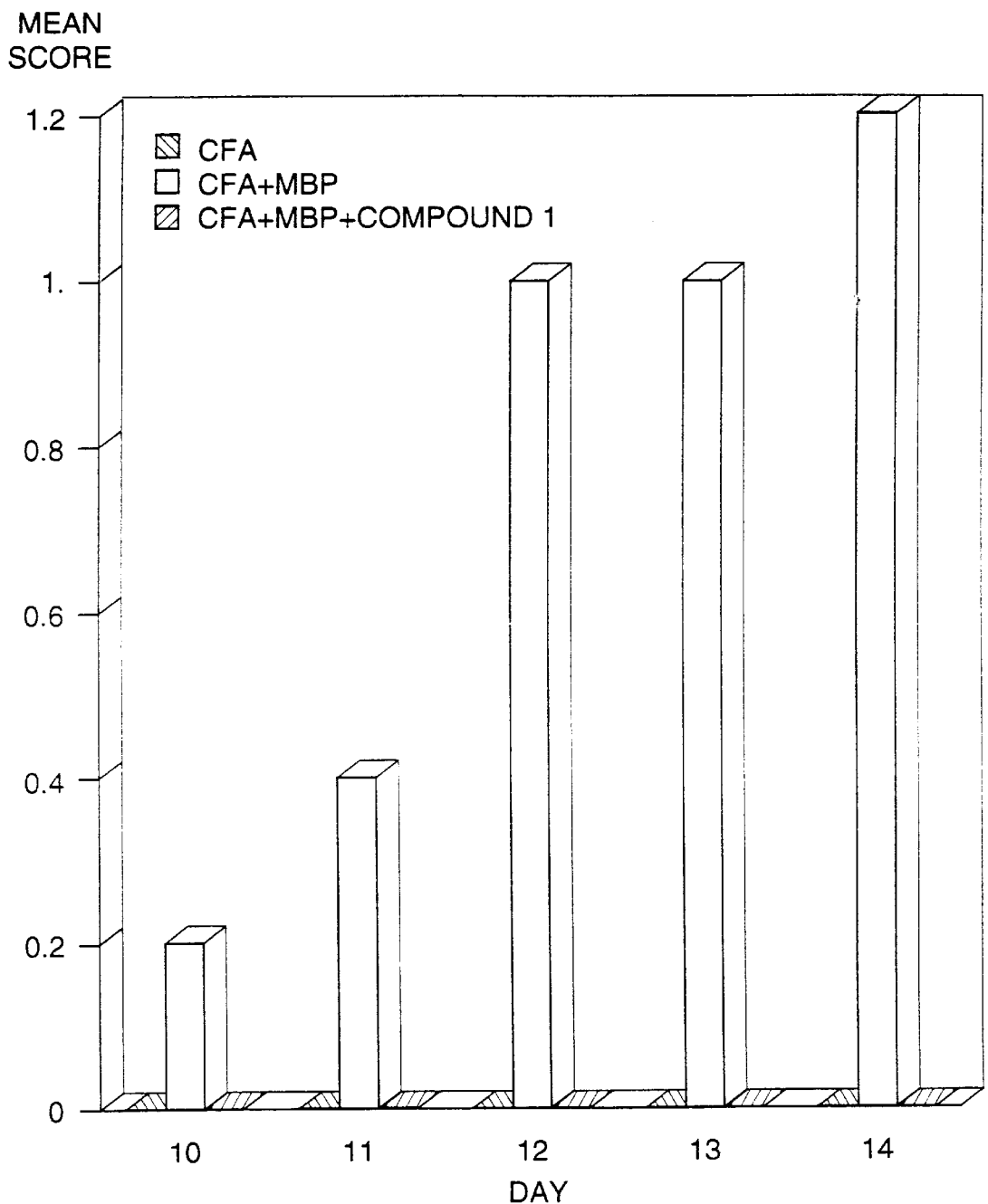
FIG. 4 is a series of bar graphs illustrating the daily behavioral scores for rodents treated with myelin basic protein (MBP), myelin basic protein (MBP) and a furan nitrone of formula I (Compound 1), or a control. The behavioral scores shown were obtained 10 to 14 days after treatment.

The results are shown in FIG. 4. These results show that N-isopropyl-α-(2-sulfofuran-5-yl)nitrone sodium salt completely counteracted the effect of MBP in this test.

Example 28

Prevention of Weight Loss

Figure 5:
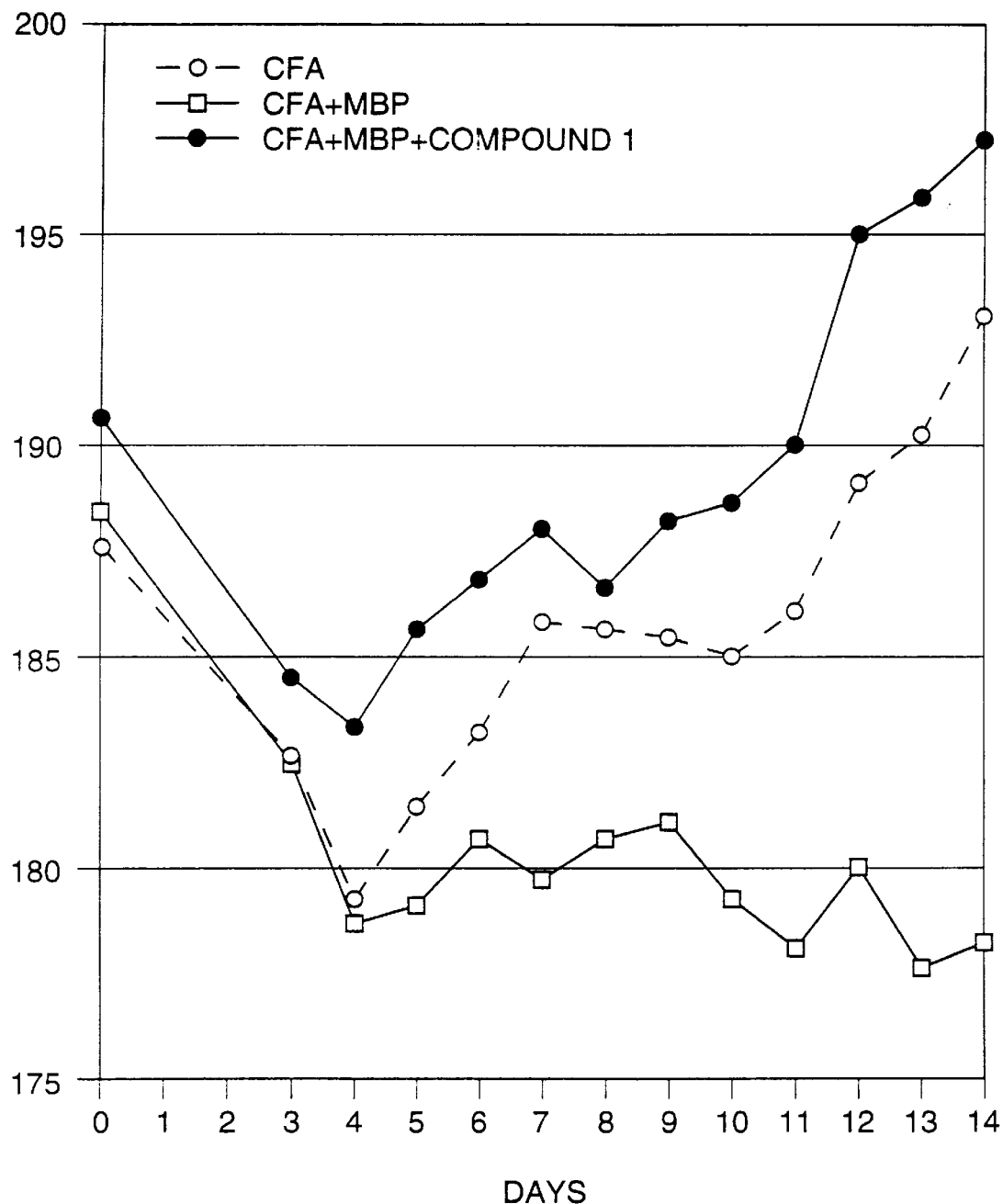
FIG. 5 is a graph showing the weight change, over a 14 day period, for rodents treated with myelin basic protein (MBP), myelin basic protein (MBP) and a furan nitrone of formula I (Compound 1), or a control.

Animals exposed to MBP or MBP peptide exhibit significant weight loss as compared to controls exposed to Freund's adjuvant alone. To determine if the furan nitrones of formula I prevented such weight loss, the animals in the EAE model described in Example 27 above were weighed daily. The results show that those animals receiving N-isopropyl-α-(2-sulfofuran-5-yl)nitrone sodium salt exhibited normal or above normal weight gain whereas the animals receiving MBP without the furan nitrone showed serious weight loss. These results are shown in FIG. 5.

Example 29

Reduction of Learning Deficit in Autoimmune Mice

In this experiment, the ability of a furan nitrone of formula I above to reduce learning deficiencies in autoimmune mice is demonstrated. Male MRL/MpJ controls and Fas$^{lpr}$ mutation mice were either dosed orally with 1% methylcellulose ("MC") or with 100 mg/kg of N-isopropyl-α-(2-sulfofuran-5-yl)nitrone sodium salt (prepared in Example 1 above) ("test compound") in 1% methylcellulose for 9–10 weeks. Following dosing, animals of approximately 4 months of age were tested in an active avoidance T-maze. In the one day test, animals were analyzed for acquisition to avoid shock within the first five trials of the test. When two experiments were combined (n=14–15), animals administered N-isopropyl-α-(2-sulfofuran-5-yl) nitrone sodium salt showed a 50% protection in acquisition learning deficit compared to Fas mutated animals receiving only 1% methylcellulose as shown in Table II.

TABLE II

| Mean Acquisition Values (Maximum score of 5.0) | | |
|---|---|---|
| Control/ 1% MC[1] | Fas$^{lpr}$/ 1% MC | Fas$^{lpr}$/Test Compound[2] |
| Mean = 2.13 | Mean = 0.857 | Mean = 1.467 |
| n = 15 | n = 14 | n = 15 |

[1]MC = methyl cellulose.
[2]The test compound was N-isopropyl-α-(2-sulfofuran-5-yl)nitrone sodium salt.

The results shown in Table II demonstrate that N-isopropyl-α-(2-sulfofuran-5-yl)nitrone sodium salt reduces the learning deficiencies developed in autoimmune mice.

From the foregoing description, various modifications and changes in the compositions and methods of this invention will occur to those skilled in the art. All such modifications coming within the scope of the appended claims are intended to be included therein.

What is claimed is:

1. A process for preparing a compound of formula I:

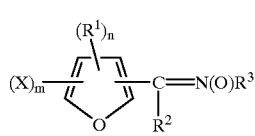

I wherein
   each $R^1$ is independently selected from the group consisting of hydrogen, alkyl, substituted alkyl, alkenyl, alkynyl, alkaryl, aryl, alkoxy, alkcycloalkyl, cycloalkyl, cycloalkenyl and halo;
   $R^2$ is selected from the group consisting of hydrogen, alkyl, substituted alkyl, alkenyl, alkynyl, alkaryl, aryl, alkcycloalkyl, cycloalkyl and cycloalkenyl;
   $R^3$ is selected from the group consisting of alkyl, substituted alkyl, alkenyl, alkynyl, alkaryl, alkcycloalkyl, cycloalkyl and cycloalkenyl;
   each X is independently selected from the group consisting of $-SO_3Y$, $-S(O)R^4$, $-SO_2R^5$ and $-SO_2NR^6R^7$;
   wherein Y is hydrogen or a pharmaceutically acceptable cation;
   $R^4$ is selected from the group consisting of alkyl, substituted alkyl, alkenyl, alkynyl, alkaryl, aryl, alkcycloalkyl, cycloalkyl and cycloalkenyl;
   $R^5$ is selected from the group consisting of alkyl, substituted alkyl, alkenyl, alkynyl, alkaryl, aryl, alkcycloalkyl, cycloalkyl and cycloalkenyl;
   $R^6$ and $R^7$ are independently selected from the group consisting of hydrogen, alkyl, substituted alkyl, alkenyl, alkynyl, alkaryl, aryl, alkcycloalkyl, cycloalkyl and cycloalkenyl; or $R^6$ and $R^7$ together with the nitrogen atom to which they are attached can form a heterocyclic ring containing from 2 to 8 carbon atoms and optionally from 1 to 3 additional heteroatoms selected from the group consisting of oxygen, nitrogen and sulfur;
   m is an integer from 1 to 3; and n is an integer from 0 to 2, provided that m+n=3, said process comprising reacting a furan carbonyl compound of the formula:

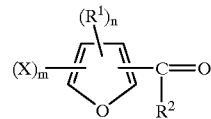

with a hydroxylamine of formula V:

$$HO-NH-R^3 \qquad\qquad V$$

to provide a compound of formula I.

2. The process according to claim 1 wherein $R^1$ is hydrogen.

3. The process according to claim 1 wherein $R^2$ is hydrogen.

4. The process according to claim 1 wherein $R^3$ is selected from the group consisting of alkyl, alkaryl, and cycloalkyl.

5. The process according to claim 4 wherein $R^3$ is alkyl or cycloalkyl.

6. The process according to claim 1 wherein X is $-SO_3Y$.

7. The process according to claim 1 wherein X is $-SO_2NR^6R^7$, wherein $R^6$ and $R^7$ are independently selected from the group consisting of hydrogen, alkyl and cycloalkyl; or $R^6$ and $R^7$ are joined together with the nitrogen atom to which they are attached to form a heterocyclic ring having 4 to 6 carbon atoms.

8. The process according to claim 7 wherein $R^6$ is hydrogen and $R^7$ is selected from the group consisting of hydrogen, alkyl and cycloalkyl.

9. The process according to claim 1 wherein X is —SO$_2$R$^5$, wherein R$^5$ is selected from the group consisting of alkyl, cycloalkyl and aryl.

10. The process according to claim 1 wherein m is 1.

11. A process for preparing a sulfamoyl-substituted furan nitrone of formula I':

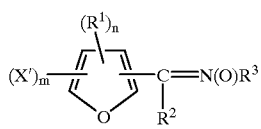

wherein each R$^1$ is independently selected from the group consisting of hydrogen, alkyl, substituted alkyl, alkenyl, alkynyl, alkaryl, aryl, alkoxy, alkcycloalkyl, cycloalkyl, cycloalkenyl and halo;

R$^2$ is selected from the group consisting of hydrogen, alkyl, substituted alkyl, alkenyl, alkynyl, alkaryl, aryl, alkcycloalkyl, cycloalkyl and cycloalkenyl;

R$^3$ is selected from the group consisting of alkyl, substituted alkyl, alkenyl, alkynyl, alkaryl, aryl, alkcycloalkyl, cycloalkyl and cycloalkenyl;

each X' is —SO$_2$NR$^6$R$^7$; wherein R$^6$ and R$^7$ are independently selected from the group consisting of hydrogen, alkyl, substituted alkyl, alkenyl, alkynyl, alkaryl, aryl, alkcycloalkyl, cycloalkyl and cycloalkenyl; or R$^6$ and R$^7$ together with the nitrogen atom to which they are attached can form a heterocyclic ring containing from 2 to 8 carbon atoms and optionally from 1 to 3 additional heteroatoms selected from the group consisting of oxygen, nitrogen and sulfur;

m is an integer from 1 to 3; and n is an integer from 0 to 2, provided that m+n=3, said process comprising the steps of:

(a) reacting a carbonyl-substituted furan sulfonic acid compound of the formula:

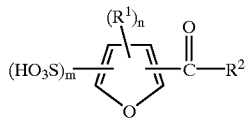

with phosphorous trichloride and phosphorous pentachloride to provide a gem-dichloride-substituted furan sulfonyl chloride compound of the formula:

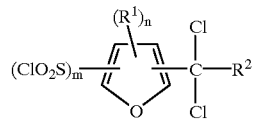

(b) reacting the gem-dichloride-substituted furan sulfonyl chloride compound with an amine of the formula:

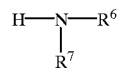

to provide a gem-dichloride-substituted furan sulfonamide compound of the formula:

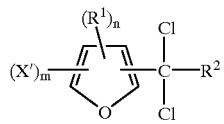

(c) hydrolyzing the gem-dichloride-substituted furan sulfonamide compound to provide a carbonyl-substituted furan sulfonamide compound of the formula:

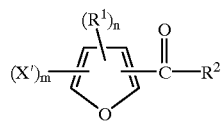

and;

(d) reacting the carbonyl-substituted furan sulfonamide with a hydroxylamine of the formula:

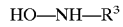

to provide a compound of formula I'.

12. The process according to claim 11 wherein R$^1$ is hydrogen.

13. The process according to claim 11 wherein R$^2$ is hydrogen.

14. The process according to claim 11 wherein R$^3$ is selected from the group consisting of alkyl, alkaryl, aryl and cycloalkyl.

15. The process according to claim 14 wherein R$^3$ is alkyl or cycloalkyl.

16. The process according to claim 11 wherein R$^6$ is hydrogen and R$^7$ is selected from the group consisting of hydrogen, alkyl and cycloalkyl.

* * * * *